(12) United States Patent  
Hasulak

(10) Patent No.: US 8,914,118 B2  
(45) Date of Patent: Dec. 16, 2014

(54) SYSTEMS, DEVICES, AND METHODS FOR MONITORING AND ANALYZING RESEARCH ANIMAL BEHAVIOR BEFORE, DURING AND AFTER BRAIN ELECTRICAL STIMULATION

(75) Inventor: Nicholas Robert Hasulak, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 261 days.

(21) Appl. No.: 13/310,571

(22) Filed: Dec. 2, 2011

(65) Prior Publication Data

US 2012/0143280 A1    Jun. 7, 2012

Related U.S. Application Data

(60) Provisional application No. 61/419,795, filed on Dec. 3, 2010, provisional application No. 61/424,612, filed on Dec. 17, 2010.

(51) Int. Cl.
*A61N 1/36* (2006.01)
*A61N 1/05* (2006.01)

(52) U.S. Cl.
CPC ............ *A61N 1/0534* (2013.01); *A61N 1/0539* (2013.01); *A61N 1/36017* (2013.01); *A61N 1/36025* (2013.01)
USPC .......................................................... 607/45

(58) Field of Classification Search
USPC .............................................. 439/625; 607/45
See application file for complete search history.

(56) References Cited

U.S. PATENT DOCUMENTS

| 3,323,134 A * | 6/1967 | Swyers ............................ 2/415 |
| 2007/0089480 A1 * | 4/2007 | Beck .......................... 73/12.01 |

\* cited by examiner

*Primary Examiner* — Alyssa M Alter  
(74) *Attorney, Agent, or Firm* — Arent Fox LLP

(57) ABSTRACT

Described are systems, devices and methods for facilitating the delivery of stimulation to, and the monitoring and recording of physiological signals (e.g., electroencephalographic signals) from a research subject. Devices include a headmount that includes a cranial frame and a headstage, and a connection between the headmount and external equipment used for stimulation, monitoring, and/or recording that is robust physically and electrically to optimize stimulation, monitoring and recording even while the subject remains ambulatory. In some embodiments, a hinged headmount allows the configuration to be easily manipulated during attachment and any subsequent adjustment or reattachment procedures and permits easy access to any wires or other components implanted in the subject. In some embodiments, a flexible cable extends out from the headmount at an acute angle relative to a horizontal plane of the headmount, to optimize strain relief as the subject moves about while attached to any stimulation, monitoring and/or recording equipment.

17 Claims, 39 Drawing Sheets

SYSTEMS, DEVICES, AND METHODS FOR MONITORING AND ANALYZING RESEARCH ANIMAL BEHAVIOR BEFORE, DURING AND AFTER BRAIN ELECTRICAL STIMULATION

REFERENCE TO RELATED APPLICATIONS

This application claims priority to and benefit of U.S. provisional patent application Ser. Nos. 61/419,795 and 61/424,612 filed Dec. 3, 2010 and Dec. 17, 2010, respectively. The provisional application corresponding to U.S. Ser. No. 61/424,612 is provided in the Appendix.

GOVERNMENT CONTRACTS

Embodiments of this invention were made with United States Government support under ATP Award No. 70NANB7H7001 awarded by the National Institutes of Standards and Technology (NIST) and NINDS Award No. 1U01NS064049-01A1 awarded by the National Institutes of Health. The United States Government has certain rights in this invention.

APPENDIX

Included herewith is an Appendix, the contents of which are considered to be included in the specification of this patent application.

FIELD

The embodiments of the systems, methods and devices disclosed herein relate to delivering stimulation to, and monitoring and analyzing research animal behavior, before during and after stimulation is delivered to neural tissue of research subjects.

BACKGROUND

Epileptic seizures are associated with excessive or abnormally synchronous neuronal activity. Physicians have been able to treat epilepsy by surgery to resect one or more brain portions or by medication. Brain surgery is irreversible, and may be ineffective or associated with neural morbidity in a sizable percentage of cases. In many instances, medication may be ineffective in controlling seizures, or patients may suffer from debilitating side effects. A more promising method of treating patients having epileptic seizures is by electrical stimulation of the brain.

Systems, devices and methods for delivering electrical stimulation through electrodes are under investigation for use in treating epilepsy, as well as a number of other conditions, including chronic pain, cardiac arrhythmias, and the like. Research equipment and associated tools are useful in furthering investigations before clinical trials are initiated in humans. It may be desirable to provide one or more improvements to the systems, devices and methods used with non-human subjects in order to carry out the research.

SUMMARY

Described here are systems, devices and methods for monitoring and analyzing the physical behavior and electrical brain activity of research animals before, during and after electrical stimulation is delivered to the brains of the animal subjects.

For each subject, an electrical recording and stimulation system may be provided for use with a specially-designed research animal enclosure to facilitate monitoring of the subject's physical behavior (via a camera and controlled illumination for video recording), monitoring of electrical data from the subject's brain (with two bipolar electrodes implanted in the subject's brain and two screw electrodes screwed into the rat's skull), and delivering electrical voltage or current stimulation to the subject's brain (through one or both of the bipolar electrodes), all the while allowing the animal to be ambulatory.

A headmount may be provided to secure electrodes and their associated leads and wires to the subject's head. Embodiments of the headmount include a cranial frame, which is fixed to the subject's cranial bone, and a headstage, which may include at least one circuit board and may be manipulable relative to the cranial frame, for example, by reason of the headstage being connected to the cranial frame via a hinge. The headstage may be detachable from the cranial frame to, for example, allow the headstage to be replaced or reused in a different subject. The headstage may be configured to accommodate or may be provided with one or more connectors for establishing electrical connectivity with the circuit board(s).

Embodiments of a headmount assembly include a cranial frame to provide structural support, a headstage configurable with a circuit board to establish connectivity between the headmount and one or more electrodes implanted in the subject, which communication may be bidirectional. The headmount may include a lower portion and an upper portion connected by at least one hinge so that the upper portion can be pivoted upward and away from the lower portion to provide a user with access to any circuit board associated with the headstage and to any wires, leads or other components that may be implanted in the subject's cranium. The lower portion may include a hollow interior in which connections to the one or more electrodes may be made. The headmount assembly may include a flexible cable associated with and extending from the headstage at an angle (for example, an angle that will be less than 90 degrees from a horizontal plane through the top of the subject's head when the headmount assembly is installed). A distal end of the flexible cable may be attached to the headstage and a proximal end attached to one or more connectors. The flexible cable may be configured to provide electrical connectivity between the circuit board(s) and the one or more connectors.

DESCRIPTION OF THE EMBODIMENTS

Elements of the electrical recording and stimulation system and of the specially-designed enclosure will now be described with reference to the accompanying figures. In addition, a copy of a presentation corresponding to some embodiments is included in the Appendix.

Figure 1:
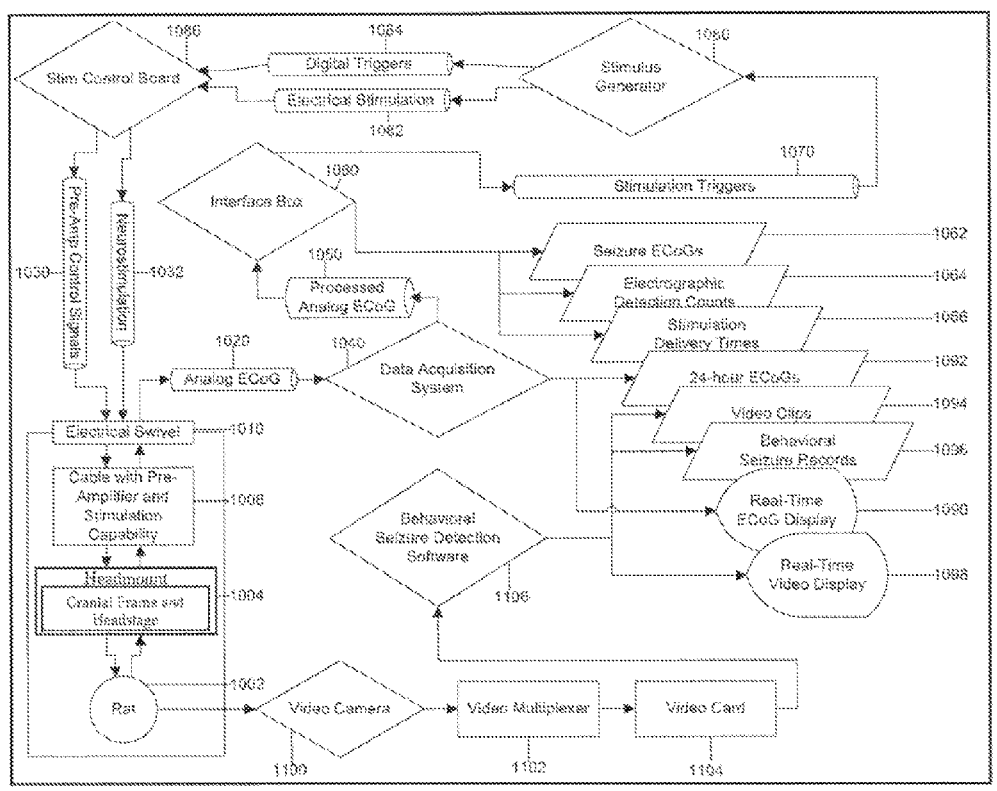
FIG. 1 is a block diagram representing the components of some embodiments of a system for monitoring and analyzing research animal behavior.

Referring now to the block diagram of FIG. 1, embodiments of a system 1000 include components and equipments that are physically or otherwise operably associated with a research subject, such as, but not limited to, the rat 1002 shown in FIG. 1. The rat 1002 is restrained insofar as it is detachably tethered to one or more cables, leads or conductive wires through which physiological signals sensed from the subject (e.g., electroencephalographic (EEG) signals can be communicated to monitoring and recording components and through which stimulation signals (e.g., voltage or current) can be delivered to neural tissue (i.e., the brain) of the rat 1002. In FIG. 1, the sensed signals are represented by the block 1020 labeled "Analog ECoG." An ECoG signal is an electrocorticographic signal and is a type of EEG signal. Unless otherwise expressly used differently, ECoG signal is used herein to refer to a signal corresponding to electrical activity of the brain that is sensed from inside the cranium (e.g., on or in the subject's brain) as opposed to a signal that is sensed through the skull (e.g., with scalp or screw electrodes). In FIG. 1, signals related to the stimulation are represented by the block 1032 labeled "Neurostimulation" and the block 1030 labeled "Pre-Amp Control Signals."

Several components facilitating sensing of physiological signals from and delivery of stimulation to the rat 1002 including (1) a headmount 1004 which is comprised of a cranial frame and headstage (the cranial frame and the headstage are not shown as separate elements in FIG. 1); (2) a pre-amp cable 1008 (also known as "cable with pre-amplifier and stimulation capability") associated with electronics including amplifiers for boosting the sensed signals before they are introduced to a data acquisition system 1040 and through which the stimulation is delivered (sometimes referred to in short hand as the "pre-amp cable"), and (3) an electrical swivel (or commutator) 1010. Each of these components is described in more detail below.

The physiological signals sensed from the subject 1002 are processed by data acquisition system 1040 (which also may be referred to as a data acquisition and control system 1040). The data acquisition system is configured to accept and recognize the signals sensed from the subject 1002, in the embodiments illustrated in FIG. 1, after the analog ECoGs have been boosted by the amplifiers in the pre-amp cable 1008. In some embodiments, the data acquisition and control system 1040 is a commercially available device sold by Pinnacle Technologies, Inc. under the name "Data Acquisition and Conditioning System" (Part No. 8206). Preferably, whichever data acquisition and control system is used, the data acquisition system 1040 can be configured to, inter alia, record and display the signals sensed from the subject 1002 in real time (with or without first processing them to reduce noise or other artifacts and before or after the signals have been amplified by the amplifiers in any pre-amp cable 1008). This real time ECoG display function of the data acquisition system 1040 corresponds to the block 1090 in FIG. 1.

The data acquisition system 1040 also preferably can be configured to cause continuously monitored ECoG signals to be recorded over long periods of time, such as 24-hour periods of time, and stored based on such periods, so that they can be retrieved and correlated with the day or consecutive days over which the signals were acquired. This function of recording and storing ECoG signals based on 24-hour periods, over successive 24-hour periods corresponds to the block 1092 in FIG. 1.

In some embodiments, a set of video components can be provided and configured to allow real time video of the research subject 1002 The set of video components include a video camera 1100, a video multiplexer 1102 associated with the video camera 1100, a video card 1104 associated with the video camera that converts the video into a digital format, and behavioral seizure detection software 1006 which accepts the digitally formatted video from the video card 1104 and uses vision-based algorithms in an effort to identify seizure behavior in the subject 1002. One example of behavioral seizure detection software 1106 that is suitable for use with some embodiments is the software sold under the name "SEIZURE SCAN" by the CleverSys, Inc. One possible output of the behavioral seizure detection software 1106 is a set of behavioral seizure records, which are represented by the block 1096 in FIG. 1.

The function of a real time video display is represented by the block 1092 in FIG. 1. In addition, the set of video components desirably is configurable to acquire, store and make available for playback video clips of the research subject 1002 over one or more time periods so that the video clips can be associated with ECoG recordings. These functions of acquiring, storing and making available for playback video clips are represented by the block 1094 in FIG. 1.

After the physiological signals sensed from the subject, analog ECoG signals 1020 in the embodiments of FIG. 1, are processed, including DC-coupling the signals and scaling the signal amplitude, by the data acquisition system 1040, the processed analog ECoG signals 1050 are introduced to an interface box 1060. In some embodiments, the interface box 1060 is provided with circuitry configured to adapt signals that are output from the data acquisition system 1040 so that they can be recognized and used by detection algorithms in the interface box 1060. Such adaptation may include high pass filtering to eliminate any undesirable DC component in incident signals, and attenuating the incident signals so that they are at a level the detection algorithms can use (e.g., without saturating or otherwise overloading any of the electronics of the interface box 1060).

More particularly, in some embodiments, the interface box 1060 allows the signals originating from the subject 1002 to be analyzed by one or more detection algorithms, on one or more channels, for example, to look for patterns in the morphological characteristics of the monitored signal or changes in the signal during certain periods of time.

The interface box 1060 may be designed to emulate the "event detection" capabilities of a neurostimulator used in an investigational system manufactured by NeuroPace, Inc. under the name "RNS SYSTEM." For example, the interface box 1060 may be configured to digitize incident analog ECoG signals and then identify when the power of the signal appears to be concentrated in one or more frequency bands (such as the half-wave detection methods described, for example, in U.S. Pat. No. 6,810,285 to Pless et al. for "Seizure Sensing and Detection Using an Implantable Device" filed Jun. 28, 2001 and issued Oct. 26, 2004). It will be appreciated that when a sensed signal has power concentrated in a particular frequency band, inferences may be made as to whether the monitored electrical activity represents some indication of a seizure, or of a seizure onset or of some precursor to a seizure onset or seizure.

Additionally or alternatively, the interface box 1060 may be configured to digitize incident analog ECoG signals and then identify whether a continuously monitored signal is changing in the short term relative to a longer term trend (which may be a fixed baseline or threshold or a dynamic trend based on signal averaging for some period of time before the short term trend is calculated). This "line length" or fractal dimension type of detection algorithm is described, inter alia, in U.S. Pat. No. 6,810,285. It will be appreciated that when the "line length" of a signal measured in this fashion increases rapidly relative to a longer term trend, the increase may be an indication of a change in the brain's electrical activity, such as a seizure.

Still additionally or alternatively, the interface box 1060 may be configured to determine in a digitized version of a sensed signal the area between the ECoG signal and a baseline within a given time frame or time window, typically relative to a threshold or dynamic trend (again, see U.S. Pat. No. 6,810,285). As is the case with the "line length" algorithm, when the "area" tool evidences a sharp increase in area (which may be thought of loosely as a stand-in for the energy of the signal) as compared to the immediately preceding average area, it may be assumed that something different is happening in the continuously monitored signal originating from the brain of the subject 1002.

The detection algorithms or tools which may be applied to incident analog ECoG signals after these signals have been acquired from the subject 1002 and processed by the data acquisition system 1040 can be used independently or in combination with each other in order to decide when patterns or conditions are present in the monitored signal that should trigger a form of electrical stimulation in response to the occurrence of the patterns or conditions. (When an algorithm determines or a collection of algorithms determine that a particular pattern or condition is occurring in a monitored ECoG, that determination is sometimes referred to as an "event detection".)

Outputs of the interface box 1060 may include digitized portions corresponding to sensed ECoGs that relate to one or more patterns or conditions (e.g., one or more detected events), including but not limited to events that are believed to correspond directly to the occurrence of an electrographic and/or clinically-observable seizure in the research subject 1002. This potential output of the interface box 1060 is represented by the block 1062 in FIG. 1.

Outputs of the interface box 1060 may also include one or more values that correspond to a number of times any pattern or condition that the interface box 1060 is programmed to detect occurs, or some subset of the number of detected events. This possible output of the interface box 1060 is represented by the block 1064 in FIG. 1.

Outputs of the interface box 1060 further may include one or more values that correspond to the actual times and/or the number of times on which a therapy associated with a stimulation trigger 1070 (described in more detail below) was delivered to the subject 1002. These possible outputs of the interface box are represented by the block 1066 in FIG. 1.

Still another output of the interface box 1060 may be one or more stimulation triggers that correspond to block 1070 in FIG. 1. A stimulation trigger may correspond to a predetermined therapy such as one burst of current-controlled pulsatile stimulation followed by a second burst of current-controlled pulsatile stimulation that is different from or the same as the first. Alternatively or additionally, the therapy triggered by the stimulation trigger may vary based on the signal being sensed from the subject 1002, for example, to approximately match the frequency of the delivered stimulation signal to an average frequency of the signal that results in the stimulation trigger (i.e., the pattern or condition or "detected event" that causes the trigger to occur) or to be delivered based on some time delay calculated from the signal corresponding to the detected event. This ability to vary the therapy based on characteristics of the signal(s) that resulted in stimulation trigger is sometimes referred to as adaptive stimulation.

It will be appreciated that forms of stimulation other than current-controlled pulsatile stimulation may be provided, such as slow wave or low frequency stimulation (approximating a sine wave) or direct current or near-DC stimulation. It will also be appreciated that, depending on the type of stimulation comprising a given therapy, multiple parameters of the therapy may be programmable or adaptable based on the sensed physiological signal, for example and in the case of current-controlled stimulation, the number of pulses in a burst or the inverse of the pulse-to-pulse interval (frequency), the amplitude, pulse width or shape of a pulse within a burst, the number and kind of bursts that comprise a given therapy.

Whatever therapy or therapies that a given stimulation trigger 1070 triggers, the stimulation to which the therapy (ies) correspond is generated by a stimulus output generator 1080. The stimulus output generator 1080 outputs an actual stimulation signal corresponding to the block 1082 labeled "electrical stimulation" in FIG. 1. The stimulus output generator 1080 may also output another signal or signals that are used to control when and how the stimulation signal is delivered, this signal or signals correspond to the block 1084 labeled "digital triggers" in FIG. 1. In some embodiments, the stimulus output generator 1080 is a commercially available stimulus generator sold by Multichannel Systems MCS GmbH (Germany) as "Model STG4008."

The electrical stimulation 1082, along with any applicable digital triggers 1084, are introduced to a stimulation control board, represented by the block 1086 in FIG. 1. The stimulation control board 1086 is an interface that allows stimulation signals generated by the stimulus output generator 1080 to be delivered on command through one or more electrodes (which may be bipolar electrode pairs as described more fully below). The stimulation control board 1086 preferably has features that improve the isolation of the stimulation signals from the other components (e.g., the components used to sense the ECoG signals) of the system. In other words, the stimulation control board 1086 facilitates configuring the system from one that senses ECoG signals into one that delivers stimulation using some of the same electrodes that are used for sensing (e.g., such as the bipolar electrode pairs described below).

Various components that are physically located between the subject 1002, on the one hand, and the stimulation control board 1086 and the data acquisition system 1040, on the other hand, will now be described with reference to the Figures. More particularly, the headmount 1004 comprising the cranial frame and the headstage, the pre-amp cable 1008, and the electrical swivel 1010 will now be described in more detail than provided in connection with the description of the system block diagram of FIG. 1.

Figure 2A:
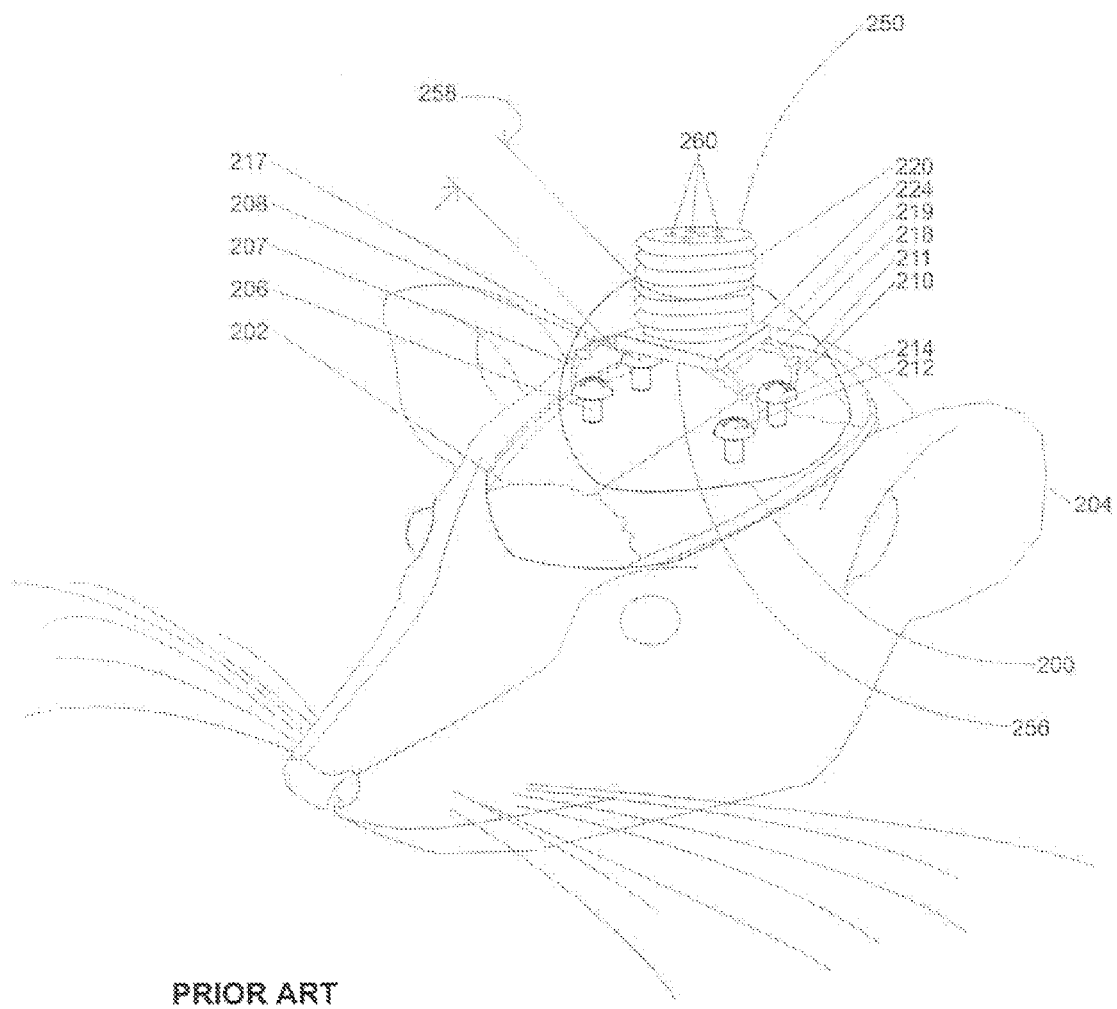
FIG. 2A is a perspective view of one example of a conventional headmount used in rats.

Referring first to FIG. 2A, one conventional headmount 200 and the manner in which it is typically established in a research subject 204 will be described. The conventional headmount 200 comprises a connector 220 mounted on a circuit board 224. The conventional connector 220 and circuit board 224 illustrated in FIG. 2A are similar to those manufactured and sold by Pinnacle Technologies, Inc. (Kansas). On a top side 250 (shown facing away from the cranium of the research subject 204 in FIG. 2A) of the connector 220, the connector 220 is provided with a plurality of receptacles 260 configured to accept wires or pins (not shown) from a cable such as a pre-amp cable that is configured to boost the physiological signals sensed from the subject corresponding to electrical activity of the subject's brain. The circuit board 224 may be a printed circuit board (PCB) that facilitates an electrical connection between one or more electrodes and the pre-amp cable. Wires 217, 218, and 219 extend from a bottom side 256 of the circuit board 224 for prospective connection to electrodes implanted in the subject's cranium 202. Alternatively, the circuit board 224 may be omitted and instead a bottom side 256 of the connector 220 may be provided with pin receptacles (not shown) for receiving pins attached to electrodes implanted in the subject's head.

One method of situating the connector 220 and circuit board 224 of FIG. 2A (sometimes referred to herein as the "connector-and-circuit-board assembly, 220 and 224") in a subject 204 and connecting it to electrodes will now be described.

The connector-and-circuit-board assembly, 220 and 224, is shown situated above an exposed portion of the cranium 202 (skull) of a rat 204. Four screw electrodes 206, 208, 210, and 212 are illustrated as having been previously implanted in the bone of the subject's cranial 202. Any of the screw electrodes 206, 208, 210, and 212 may be bare or may be provided with an electrically conductive wire already attached to the screw. In FIG. 2A, a wire 207 is shown attached to the screw electrode 206, a wire 211 is shown attached to the screw electrode 210 and a wire 214 is shown attached to the screw electrode 212. Each of the wires attached to the screw electrodes may be joined with a corresponding one of the wires extending from the bottom side 256 of the circuit board 224. In FIG. 2A, screw electrode 206 and its associated wire 207 are shown connected to circuit board 224 (e.g., PCB) and to wire 217 extending from the bottom side 256 of the circuit board 224; screw electrode 210 and its associated wire 211 are shown connected to circuit board 224 via wire 218; and screw electrode 212 and its associated wire 214 are shown connected to circuit board 224 via wire 219.

Each corresponding pair of wires 207 and 217, wires 211 and 218, and wires 214 and 219 may be attached by crimping or other appropriate means If a screw electrode is not associated with its own wire for attachment to the connector-and-circuit-board assembly, 220 and 224, then a wire extending from the bottom side 256 of the circuit board 224, such as one of the wires 217, 218, or 219 in FIG. 2A, may be wrapped by hand a number of times around the screw electrode in order to make electrical contact with it. In some methods of attaching the connector-and-circuit-board assembly, 220 and 224, to research animals, when there are twisted wire junctions between a screw electrode and a headmount, the twisted wire junction may be coated with silver epoxy in an effort to achieve a stable electrical connection.

The conventional connector-and-circuit-board assembly, 220 and 224, and methods of attaching it to the research subject 204 generally result in a considerable amount of exposed wire (for example, as a consequence of wrapping the wire around the screw) and may be challenging to use with any type of electrode other than a screw electrode (for example, the typical configuration of a twisted pair bipolar electrode makes the ends clumsy to manipulate during attachment). The conventional connector-and-circuit-board assembly, 220 and 224, and methods of attaching it also may result in poor electrical connectivity between the electrodes and any sensing or recording cables and equipment, for example, due to ineptly twisted wires, the presence of insulation around the wire that was intended to be removed during attachment, failure of the silver epoxy to provide conduction and/or failure of any crimped connections.

In a conventional method after the conventional connector-and-circuit-board assembly, 220 and 224, is connected to the screw electrodes 206, 208, 210, and 212, the conventional headmount 200 is built up around the screw electrodes 206, 208, 210, and 212, the wires 207, 211, and 214 attached to the screw electrodes, the wires 217, 218, and 219 crimped or otherwise joined to their counterparts on the screw electrodes are all built up into the conventional headmount 200 using a binder, such as dental cement (methyl methacrylate). Typically, layer upon layer of dental cement is built up on the exposed cranium 202, so that the screw electrodes 206, 208, 210, and 212 and a lower portion 258 of the connector-and-circuit-board assembly, 220 and 224, are encased in the cement. On the one hand, this process of building up the conventional headmount 200 can be relatively time consuming, since each layer must be allowed to cure partially before another layer may be deposited. On the other hand, dental cement also may be challenging to work with because it cures relatively quickly, and therefore transitions in a short period of time from a low viscosity fluid (that can run into exposed animal tissue, potentially causing inflammation and infection) to a near solid (potentially forming clumps that will not adhere well to any previously-deposited layers of cement). Once the dental cement has cured and has become a relatively hard solid, it is impossible to remedy any problems in the integrity of the electrical connections. The conventional headmount 200 cannot easily be removed from the animal and redone, nor can the components of the connector-and-circuit-board assembly 220-224 be reused with a different subject.

Figure 2B:
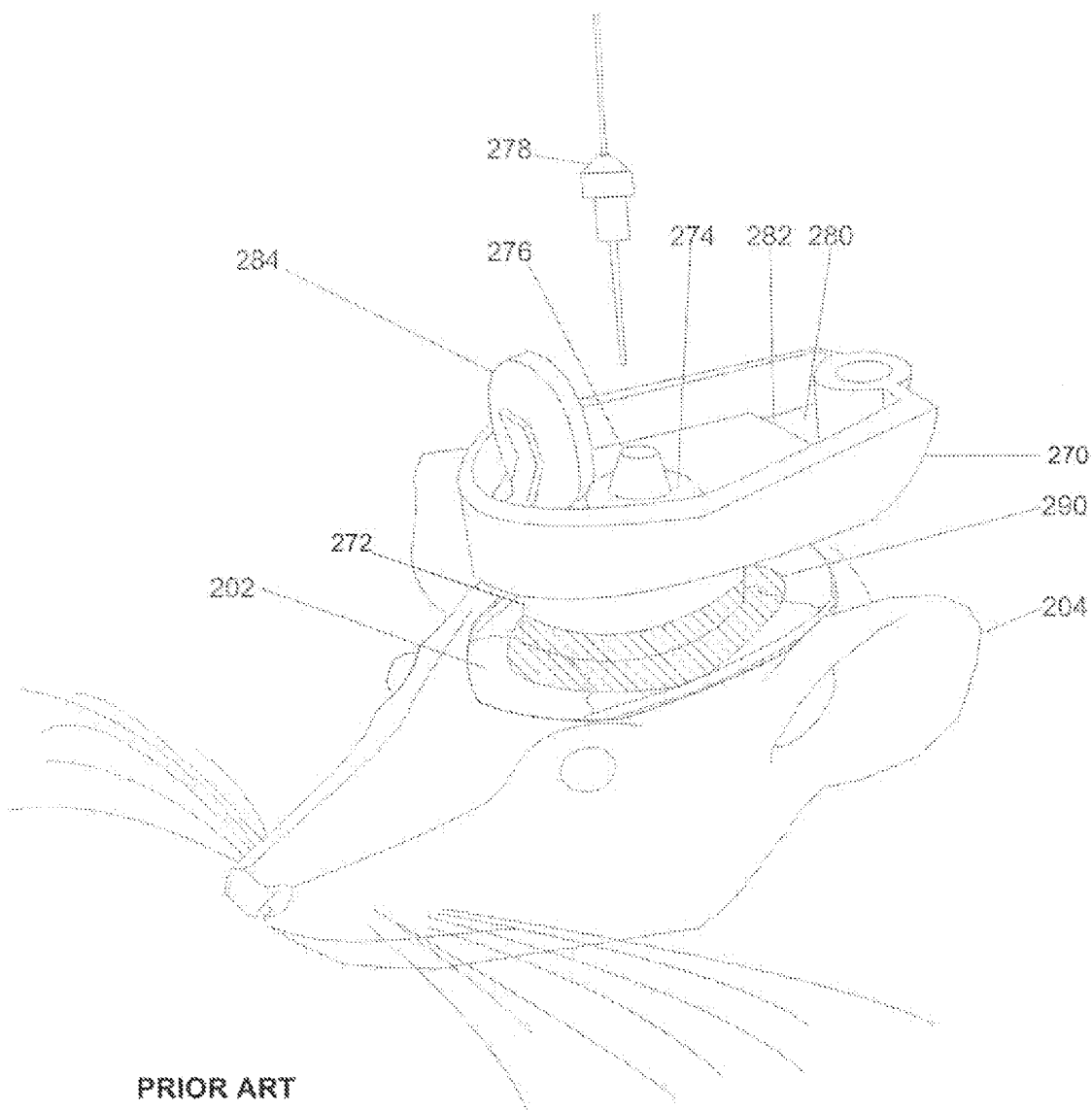
FIG. 2B is a perspective view of another example of a conventional headmount used in rats.

Referring now to FIG. 2B, another conventional headmount 270 and the manner in which it is typically established in a research subject 204 will be described. The headmount 270 comprises a lower portion 272 provided with an aperture 274 which may be configured to receive a cannula 276 which cannula 276 in turn may be adapted to receive at least one biosensor (a single biosensor 278 is shown in FIG. 2B). The lower portion 272 of the conventional headmount 270 may be formed from a plastic (e.g., by injection molding) and may be provided with a hollow interior 280 in which a circuit board 282 may be seated therein. The circuit board 282 may be provided as a PCB with traces for establishing electrical connectivity between electrodes implanted in the subject 204 and the at least one biosensor 278. Alternatively or additionally, the circuit board 282 may be provided with components (not shown in FIG. 2B) that are useful in acquiring a measurement from the subject 204 with the at least one biosensor 278 (e.g., a biosensor that is configured to sense levels of a neurotransmitter). A battery 284 is attached in the hollow interior 280 (primary cell with a correspondingly limited useful life). The limited useful life of the battery (e.g., three days or so) as well as the often limited lifetime of a typical biosensor (e.g., 6 to 72 hours after implantation), prevent this configuration from being well-suited to chronic monitoring of a subject.

The conventional headmount 270 illustrated in FIG. 2B is similar to one manufactured and sold by Pinnacle Technologies, Inc. (Kansas) and sometimes referred to as the "rat hat." Pinnacle's "rat hat" is designed for compatibility with a limited set of biosensor probes manufactured and sold by Pinnacle, and has a capacity for recording only two channels of data at a rate of one sample per second. The Pinnacle "rat hat" headmount 270 is configured for data collection only (i.e., wireless data collection using the at least one biosensor 278) and therefore the conventional headmount 270 is not suited for use with an experimental protocol that includes delivering electrical stimulation to the research animal.

In one method of affixing the conventional headmount 270 to the cranium 202 of the subject 204, a cannula 276 is inserted into the subject's cranium to provide a guide when the at least one biosensor 278 is inserted into the brain of the subject 204. The aperture 274 of the conventional headmount 270 is then positioned around an exposed portion of the cannula 276. Based on the foregoing, it can be appreciated that the goodness of the fit of the conventional headmount 270 to the subject 204 will depend in part on where the cannula 276 has been inserted. If the cannula 276 has been inserted too close to a perimeter of the exposed area of the subject's cranium 202, then when the conventional headmount 270 is fitted over the cannula, the lower portion 272 may not be able to be fitted as well as might be desired onto the cranium 202. Additionally, in order for the exposed portion of the cannula 276 to be securely accommodated in the aperture 274 of the headmount 270, the conventional headmount 270 has to be situated in a plane that is approximately orthogonal to the surface of the subject's cranium 202; otherwise, the exposed portion of the cannula 276 will not remain exposed once the conventional headmount 270 is fitted over it. It will be appreciated that if this conventional headmount 270 is used to enable chronic access with sensors to the subject's brain, the structural constraints of the conventional headmount 270 may limit may limit the areas of the brain to which access can be had. For example, access to deep brain structures that otherwise might be accomplished by implanting a deep brain electrode at a sharp angle (measured from the horizontal) through the subject's cranium.

Once the conventional headmount 270 of FIG. 2B has been fitted over the exposed portion of the cannula 276, the lower portion 272 is secured to the subject's cranium 202 with an adhesive 290, such as dental cement. An upper portion or cover (not shown in FIG. 2B) may then be fitted over the lower portion 272. After it is affixed to the cranium 202 of the subject 204, the conventional headmount 270 has a relatively large profile relative to the subject's head and overall size. This large profile may interfere with the subject's movement and other activities over the course of an experiment.

Referring now to FIGS. 3A-3E, embodiments of a headmount 300 will be described. A research subject 304 is shown with an exposed portion of its cranium 306. Two holes 310 and 312 are formed in the cranium 306. A distal portion 314 of a first twisted pair bipolar electrode 316 is shown extending out from the hole 310, where the first twisted pair is comprised of a primary twisted pair wire 320 and a secondary twisted pair wire 321. A distal portion 322 of a second twisted pair bipolar electrode 324 is shown extending out from the hole 312, where the second twisted pair is comprised of a primary twisted pair wire 326 and a secondary twisted pair wire 328. Three screw electrodes 330, 334, and 338 are shown screwed into the exposed portion of the cranium 306. Each screw electrode is provided with a wire connected to and extending therefrom: wire 332 is connected to screw electrode 330, wire 336 is connected to screw electrode 334, and wire 340 is connected to screw electrode 338. Unless otherwise expressly indicated to the contrary, all references to "wire" herein are references to something that conducts electrical signals. The wires 332, 336 and 340 may be provided from a supplier to the experimenter/user already attached to the screw electrodes 330, 334, and 338. Alternatively, the user may need to attach the wires 332, 336, and 340 to the screws by some means, such as a by a conductive epoxy or by simply wrapping a distal end of each wire around its corresponding screw electrode. A twisted pair bipolar electrode may be referred to as a "microelectrode" in order to distinguish it from screw electrodes. In some embodiments, the twisted pair bipolar electrodes are commercially available electrodes (for example, from Plastics One, Inc.) Each of the primary and secondary wires in a given twisted pair electrode may be insulated along much of its length, with a portion of bare wire exposed at a distal end (i.e., to make a connection to the subject) and at a proximal end (i.e., to make a connection to the headmount or another component of the experimental set up). Insulation along the wire may be beneficial to, for example, minimize electrical noise and to enhance mechanical stability. Each wire associated with a screw electrode similarly may be formed from a wire that is partially insulated along its length (e.g., with silicone). The conductive portion of a screw electrode wire may include nickel, so that it will be easy to solder the conductive portion to the screw electrode (or to another component at a proximal, non-insulated portion of the wire). The conductive portion of a wire may be DC-resistance welded to the screw electrodes. The screws may be formed from stainless steel.

The screw electrodes 330, 334, and 338 and the first and second twisted pair bipolar electrodes 316 and 324 may be used in various configurations (or montages) to sense electrical activity (e.g., changes in field potential between an electrode and a reference or differences in field potentials between one electrode and another electrode (such as between the primary and secondary wires comprising a twisted electrode pair)). Differential recordings may be preferred in some applications, such as when electrographic activity thought to be associated with a seizure is being analyzed, since differential recordings tend to provide more localized data (as opposed to, for example, "monopolar" recordings referenced to some other conductive element in the subject positioned at a distance from an electrode). Differential recordings between the two poles of a bipolar electrode tend to subtract out electrical signals originating distally of the distal tips of the wires and therefore provide the local field potential of only the tissue closest to the wire ends. When seizure activity is being monitored for, this aspect of differential recording may be highly desirable at least for the reason that seizures tend to be focal and originate in the hippocampi of the brain. Screw electrodes, on the other hand, when used to acquire a differential measurement, may provide information about the activity in larger volumes of neural tissue, such as electrical activity occurring inter-hemispherically or between the two hemispheres of the subject's brain. When bipolar microelectrodes and screw electrodes are used in combination for recording signals from the subject's brain, the data recorded can be used to sense both "local" and "bulk" recordings from the subject. A given electrode configuration may be referred to as a channel, for example, when the configuration is used to sense data from the subject. The field potential data sensed using a given electrode configuration or channel may be referred to as an EEG signal or an ECoG signal. The twisted pair electrodes also may be used to deliver a form of electrical stimulation to the subject. Both the sensing and stimulation functions will be described in more detail below.

A cranial frame 342 is defined by an inner surface 344 and an outer surface 346 and a frame aperture 348. In some embodiments, the cranial frame 342 is formed from an ultraviolet cured resin using a rapid prototyping device (e.g., a 3-D printer such as the 3-D printer sold under the name "ALARIS30 3-D Printer" by Objet Geometries, Ltd. This particular ultraviolet cured resin, when cured, is characterized by physical properties approximating those of ABS (acrylonitrile butadiene styrene) plastic. Alternatively, in some embodiments the cranial frame 342 may be machined from a lightweight epoxy foam to desired specifications, wherein the lightweight epoxy approximates the consistency of bone.

In some embodiments, the cranial frame 342 is characterized by a substantially rectangular shape and is further characterized by thin, low walls, and has a frame aperture 348 that approximates the perimeter of the available cranium area of the subject that is exposed during the surgery. These features are believed to maximize contact of the cranial frame 342 with the subject's skull for stability.

Generally, the size of the frame aperture 348 of embodiments are preferably optimized for the particular research application and/or research subject 304 with which the headmount 300 is to be used. For example, in an experiment in which access to the brain with multiple wires or electrodes or other biological sensor components is desired or necessary, the size of the frame aperture 348 is great enough to accommodate those components. Desirably, the frame aperture 348 is large enough to allow the researcher easy access to the site at which the components are introduced to the subject's brain and to facilitate relatively unobstructed manipulation of the same.

The cranial frame 342 includes various mounting points (such as receptacles for screws, mounting pins or hinges and the like) for attaching the cranial frame 342 to a headstage (not shown in FIG. 3A) as described below.

The cranial frame 342 is designed to be affixed to the head of the subject 304 using an appropriate means, such as using an adhesive (e.g. dental cement (methyl methacrylate), cyanoacrylate, or a two-part surgical grade epoxy for example as sold under the trade name "CEREBOND" from myNeuroLab.com). After the cranial frame 342 is affixed to the subject's head and the headmount 300 is completely installed in the subject 304, any implanted sensing or stimulation hardware (e.g., screw electrodes, bipolar microelectrodes or other components used in acquiring a sensor measurement or delivering stimulation) will be encased or sealed relative to the subject's external environment.

Figure 3A:
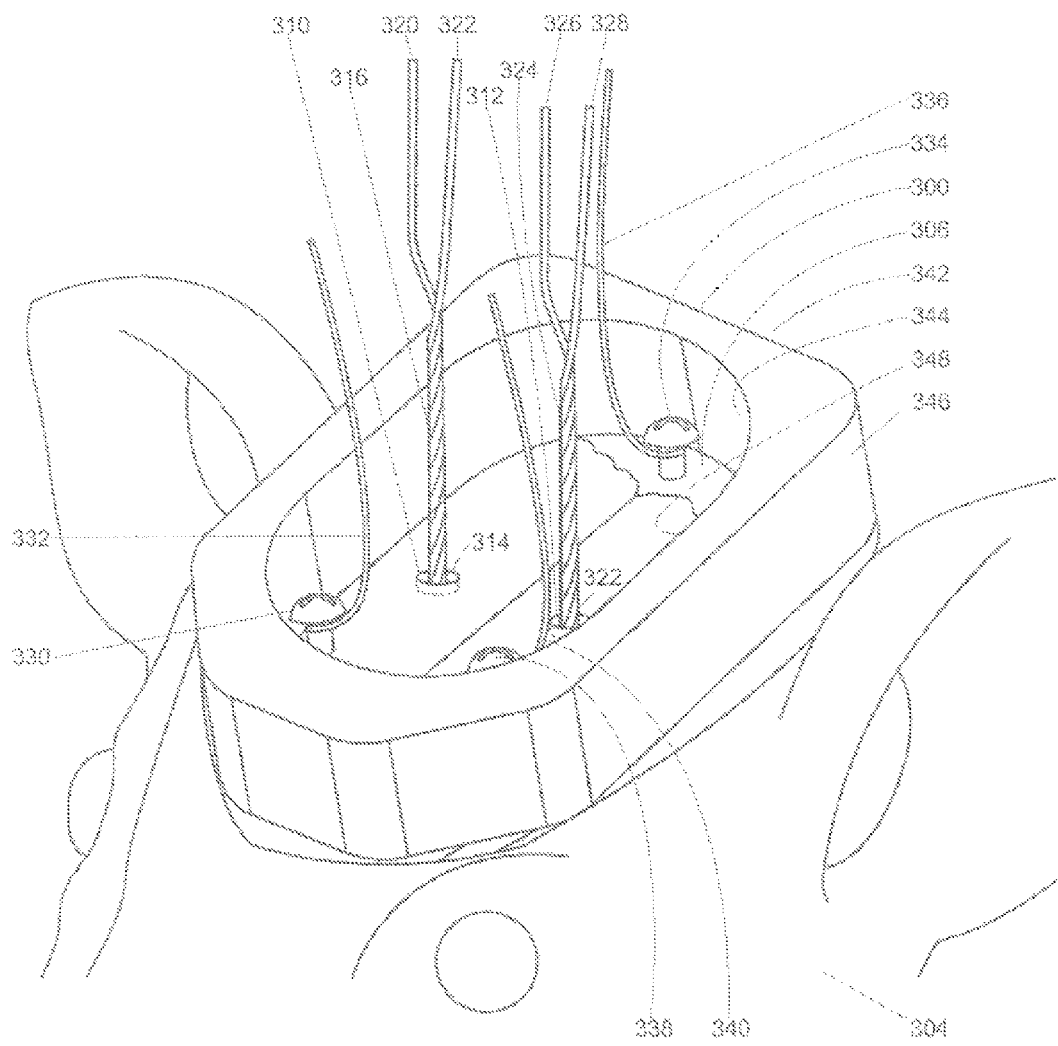
FIG. 3A is a perspective view of a cranial frame of a headmount in accordance with an embodiment.
Figure 3B:
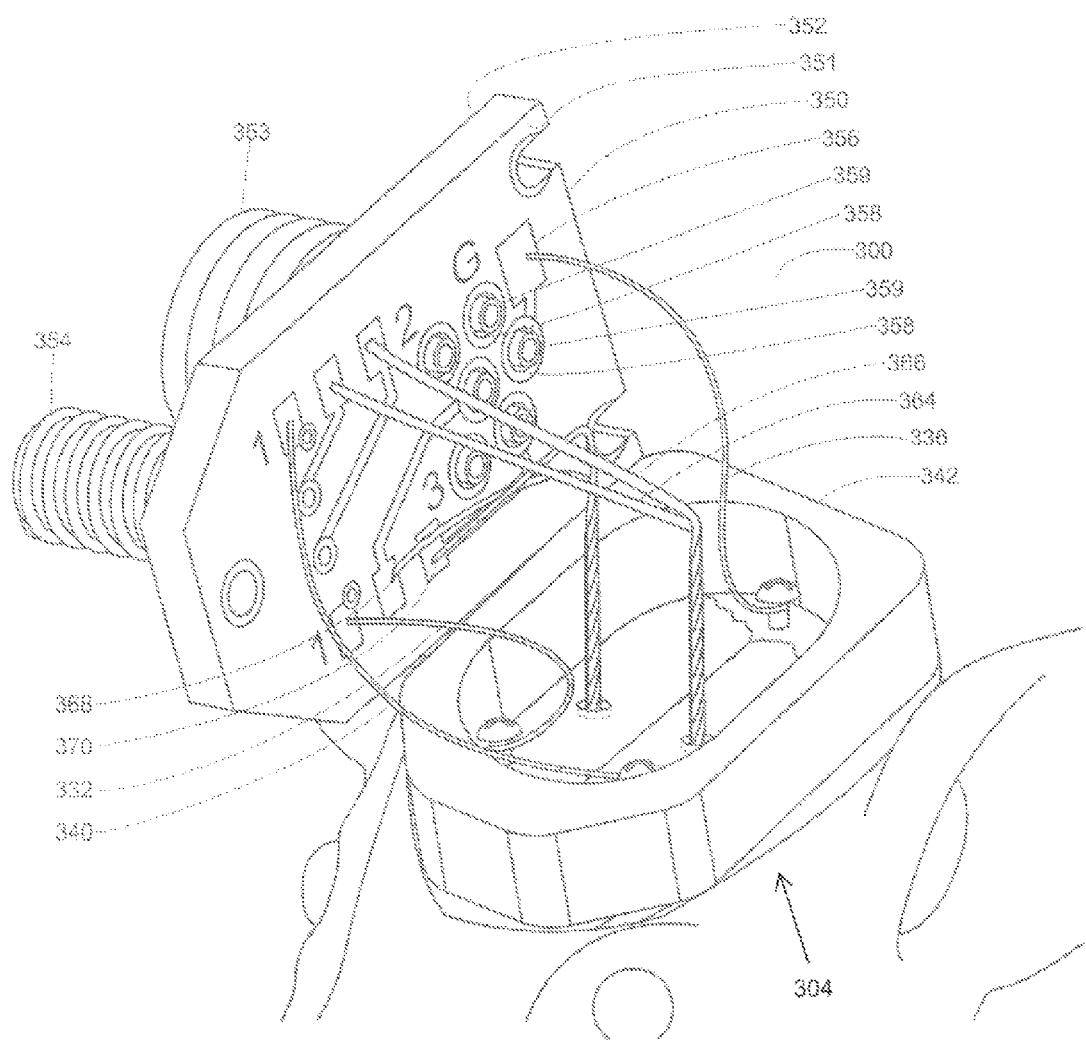
FIG. 3B is an alternate perspective view of the cranial frame of FIG. 3A with a headstage.

Referring now to FIG. 3B, a headstage 350 is shown in an open position relative to the headmount 300. The headstage 350 may be formed from the same material as the cranial frame 342 (e.g., an ultraviolet cured resin or lightweight epoxy foam) or a different material and using the same or similar methods (e.g., 3-D printer or machining). The headstage 350 is characterized by a lower surface 351 and a top surface 352. One or more connectors may be provided in the headstage 350 so that each connector will extend upwardly or away from the surface of the subject's head when the headmount 300 is installed. In FIG. 3B, a first connector 353 and a second connector 354 are shown extending out of the top surface 352 of the headstage 350. One of the first or second connectors, 353 or 354, respectively, may be provided to serve as an electrical conduit for signals from the screw electrodes 330, 336, and 338. The other of the first or second connectors, 353 or 354, respectively, may be configured to serve as an electrical conduit for signals transmitted from and to the twisted pair bipolar electrodes 316 and 324. The connectors 353 and 354 may be provided to facilitate connection between the headmount 300 and other components of an experimental system, such as the pre-amp cable 1008 and stimulation control board 1086 and the data acquisition system 1040 described with reference to FIG. 1 and further described hereinbelow. More or fewer connectors that are the same or similar to the connectors 353, 354 may be provided in some embodiments of the headstage 350 and headmount 300, for example, in order to correspond with the desired number of conductors and/or to allow connections between each electrode site/wire and another system element, such as the preamp cable 1008. For example, if a user wishes to use an additional bipolar electrode, then it may be desirable to provide the headstage 350 with a 12-pin connector such as the 12-pin connector sold under the name "Micro Latching Plastic Circular Connector" by the Omnetics Connector Corporation. Connectors or conduits for sensors configured to sense a biological or physiological signal other than an electrographic signal (e.g., voltammetry sensors, impedance plethysmography sensors, optical sensors, thermal sensors, and the like) may also be provided in embodiments of a headmount 300. The size of the frame aperture 348 may be determined in part by the number and type of sensors with which the headmount 300 is to be used and/or the degree to which the user must be able to manipulate the sensors or their related components while the headmount is being installed in the subject.

Conductive elements 356 (which may comprise traces or pads or pins or receptacles) may be provided on the lower surface 351 of headstage 350 to facilitate establishing electrical connectivity between the electrodes implanted in the subject, on the one hand, and the headmount or the other system components to which the headmount ultimately may be connected, on the other hand. Connector receptacles 358 may be provided to accommodate connector pins 359 that extend through one or more of the connectors 353 and 354 and the lower surface 351 of the headstage 350. A proximal portion 364 (i.e., a proximal portion of exposed wire from which any insulation has been removed) of the primary twisted pair wire 320 of the first twisted pair bipolar electrode 316 and a proximal portion 366 (without insulation) of the secondary twisted pair wire 321 of the first twisted pair bipolar electrode 316 are connected to separate conductive elements 356 on the lower surface 351 of the headstage 350. Proximal conductive portions 368 and 370 of each of the wires, the primary twisted pair wire 326 and the secondary twisted pair wire 328 comprising the second twisted pair bipolar electrode 324 similarly may be connected to a conductive element 356 on the headstage 350. A proximal conductive portion of each of the wires 332, 336, and 340 extending from the screw electrodes likewise are each connected to a conductive element 356 on the headstage 350. Attachment of the wires to the conductive elements 356 may be accomplished by soldering or using a conductive epoxy or by some other appropriate means of attachment.

Other embodiments of the headstage 350 may include an attached or integral circuit board (not shown in FIG. 3B) that is provided with circuitry specific to a given experimental protocol (e.g., application-specific circuitry depending on the type of sensing and signal conditioning desired). For example, a miniaturized differential pre-amplification circuit may be placed on the board.

In some embodiments, the cranial frame 342 and headstage 350 may be manufactured using a 3-D printer. The cranial frame 342 and headstage 350 first may be designed with 3-D CAD solid modeling software (such as Solidworks, sold by Dassault Systemes). The Objet30 3D Printer, when input a 3-D CAD model file, slices the model into horizontal slices about 20 microns thick. A fine inkjet-like print head deposits a UV-sensitive model resin, that when cured has properties approximating ABS plastic, onto a build tray corresponding to the positive space comprising the first slice of the model. A separate print head deposits a brittle gel-like UV-sensitive support material comprising the negative space of the first slice of the model, serving as a support layer for additional deposition of material. Multiple passes of the print heads are usually necessary to deposit a complete layer. As the heads move across the build tray, an attached UV lamp partially cures the most recently deposited layer of resin. As the print heads make subsequent passes, the build tray is lowered and additional material is deposited, each layer on top of the last. With each pass, the previously-deposited material cures until reaching full cure. Once all material is deposited and cured, the model is removed from the 3-D printer and the support material is discarded by washing the model with a high pressure water jet. This method is preferred because it allows rapid customization of the cranial frame 342 and headstage 350 based on changes in the PCB, added or removed on-board electronics, changes in the placement or shape of the connector(s), or adaptation to a different animal's cranium as the experimental needs dictate. Once a desired embodiment of the cranial frame 342 and headstage 350 is achieved, the same 3-D CAD model file or the 3-D printed model can be used as the basis for molding the parts in plastic for higher production rates.

In still other embodiments, varying configurations of components and circuit boards may be used, including but not limited to a plurality of circuit boards stacked vertically; additional components (e.g. a battery, other transducers/transmitters); and mounting platforms allowing the connection of various fragile, sensitive, or otherwise specially implanted sensors (e.g., a carbon fiber electrode, photodiodes, optical fibers, etc.). The headstage 350 preferably is attached to the cranial frame 342 with a hinge (not shown in FIG. 3B) to allow the headstage 350 to pivot relative to the cranial frame 342. In some embodiments, one half-hinge portion is provided on the cranial frame 342 and a mating half-hinge portion is provided on the headstage 350. The half-hinge portions may be provided along one side of the longer dimension of the cranial frame 342 and headstage 350, e.g., when the headmount 300 or cranial frame 342 is provided with a generally rectangular shape. A modified cranial frame 342 may be provided of appropriate size to accommodate a corresponding headstage 350 with a mated half-hinge on a corresponding edge, such that when the two are joined following attachment of the cranial frame to the skull, and a hinge pin or similar element is inserted, a hinge is formed that allows the headstage 350 to be rotated out of or swung away from the immediate surgery area while the cranial frame remains affixed to the skull (see, e.g., FIG. 6F), thus providing access to the headstage 350 without disturbing the implanted hardware, such as for the soldering of electrodes to pads on the headstage circuit board. Once satisfactory connections are made, the hinge may be rotated closed such that the base of the headstage encasement fits securely against the cranial frame and can then be secured as above (i.e., with screws, latches, etc.).

In alternative embodiments, means other than a hinge may be used to attach (removably or permanently) the headstage 350 to the cranial frame 342, such as detents, latches, pins, screws, or the like.

Figure 3C:
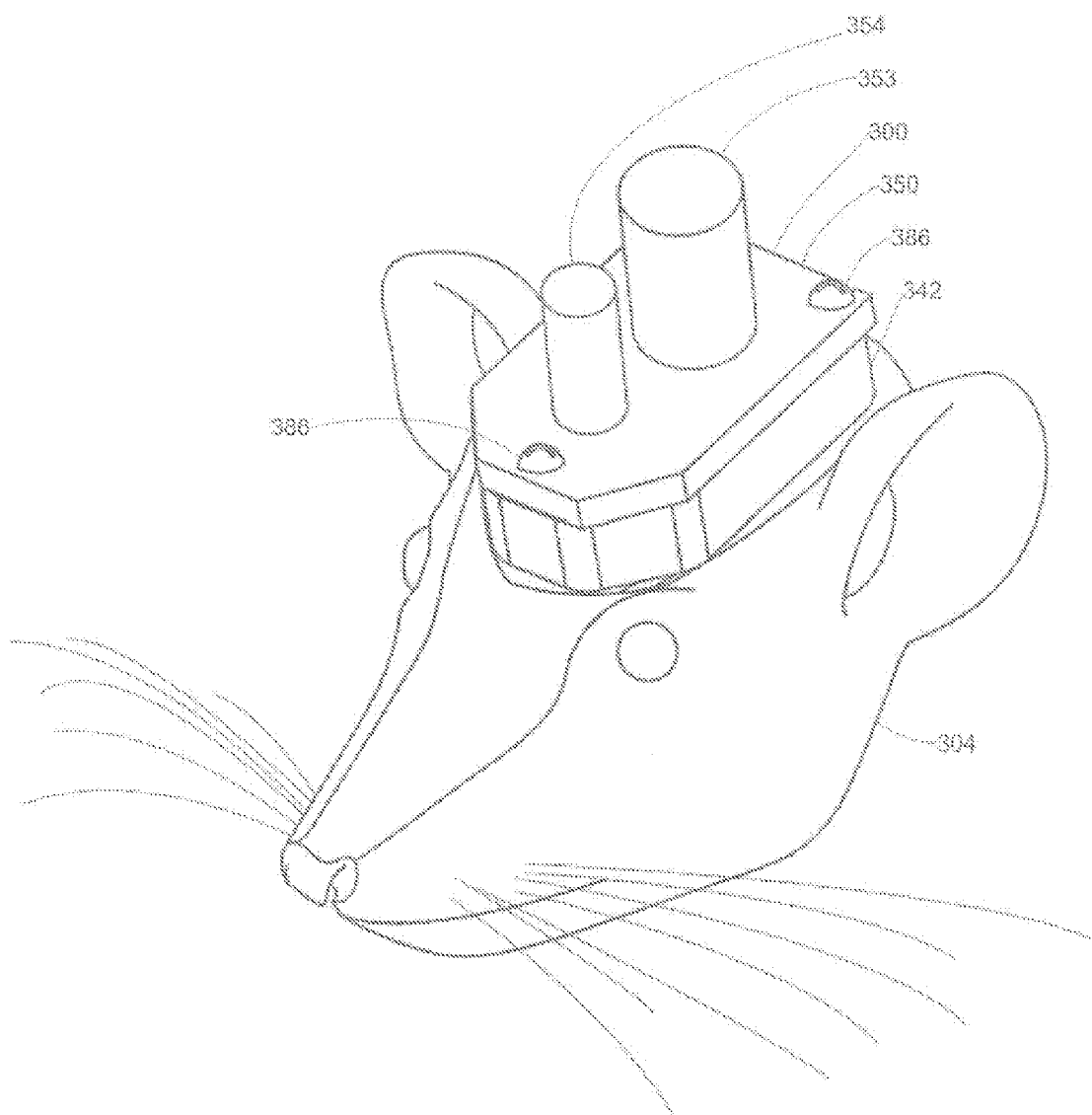
FIG. 3C is a further perspective view of the headmount of FIG. 3B.

Referring now to FIG. 3C, a headmount 300 installed in a subject 304 is illustrated. The generally rectangular cranial frame 342 and headstage 350 are joined together and secured by headstage attaching screws 386. Preferably, dental cement or some other adhesive (not shown in FIG. 3C) is used to further secure the headmount 300 to the subject at the subject's cranium 302.

Figure 3D:
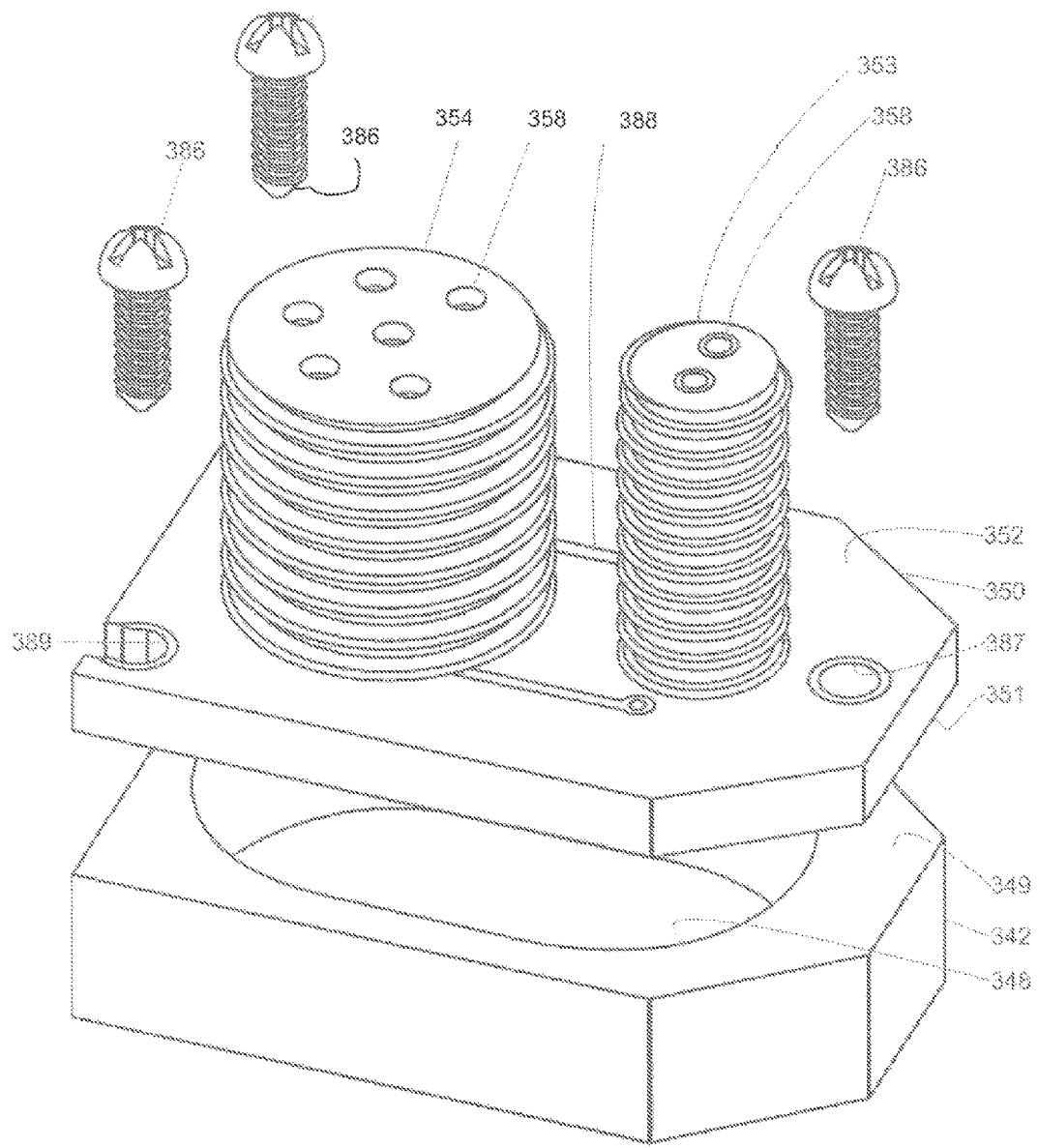
FIG. 3D is an exploded perspective view of various components of some embodiments of a headmount.

FIG. 3D is an exploded view of a headmount 300 illustrating three headstage attaching screws 386 that are used to connect the headstage 350 to the cranial frame 342. The headstage attaching screws 386 may be self-tapping, so that when they are introduced to a surface, such as a top surface 349 of the cranial frame 342, they will engage with the top surface 352. In some embodiments, a circuit board 378 may be formed integrally with the headstage 350, so that the circuit board 378 comprises an element defined by the headstage top surface 352 and the lower surface 351. A circuit board 378 of the headstage 350 is provided with conductive traces 388 that may be used to allow connections to be made between the connectors 353, 354 and other elements of a research system. One or more apertures 387 or cut-out slots 389 may be provided for receiving headstage attaching screws 386. A cut-out slot 389 provides the advantage of allowing the headstage 350 to be slid into contact with a previously attached headstage attaching screw 386.

Figure 3E:
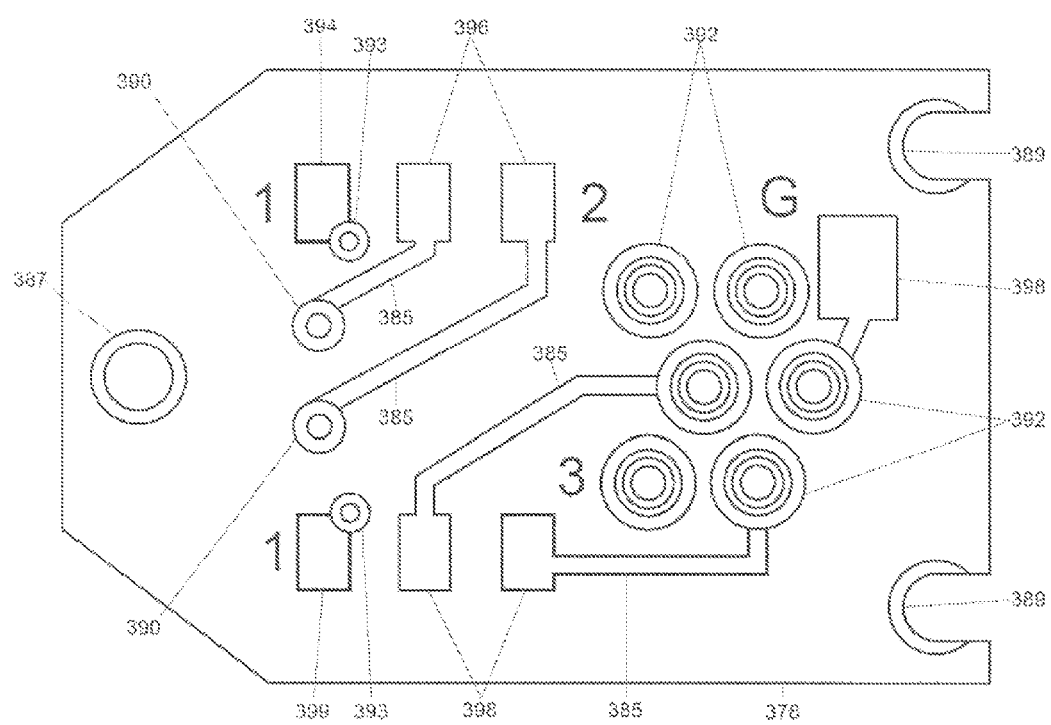
FIG. 3E is a bottom plan view of a printed circuit board in accordance with an embodiment of a headmount.

FIG. 3E is a bottom plan view of a circuit board 378 of a headstage 350 corresponding to the lower surface 351 of the headstage 350. Conductive vias 390 and 392 extend through the thickness of the circuit board 378 from the lower surface 351 through to the top surface 352 in order to provide connectivity with the connectors 353 and 354. Traces 385 on the circuit board 378 connect vias 390, 392, and 393 to pads 396, 394, 398, and 399.

It will be appreciated that embodiments of the headmount illustrated in FIGS. 3A-3E and described and illustrated elsewhere in this application may be scalable, for example, to a size suitable for a particular type of research subject (e.g., rats versus mice) or to a size suitable for a particular experimental protocol (e.g., some experimental protocols may require access to larger areas of the research subject's cranium than others; thus for those protocols the overall dimensions of the headmount or the size of the aperture provided in the cranial frame may be larger to afford greater access to the exposed portion of the cranium or to allow more room for a user to manipulate and maneuver [e.g. in placing electrodes]).

Figure 4A:
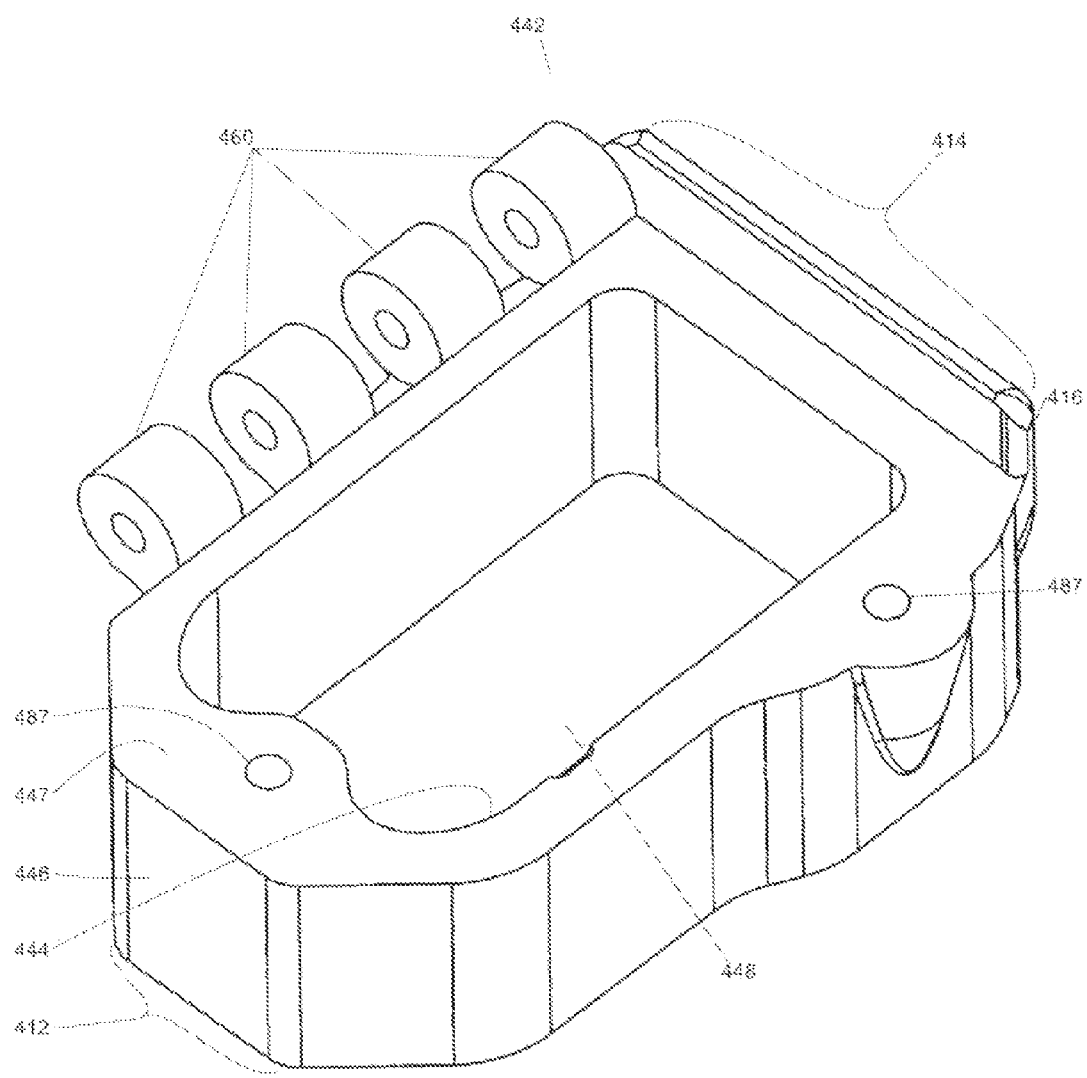
FIG. 4A is a perspective view of a cranial frame of a headmount in accordance with an embodiment.

FIGS. 4A-4E illustrate various aspects of a headmount 400 in accordance with some embodiments. Referring first to FIG. 4A, a cranial frame 442 of a headmount 400 in accordance with some embodiments that is characterized by an inner surface 444, and outer surface 446, a top surface 449, a frame aperture 448, and apertures 487 for receiving attaching screws or other elements to secure the cranial frame 442 to another component of the headmount 400, such as a headstage 450. The cranial frame 442 of FIG. 4A is characterized by an approximately rectangular shape. On a long side of the cranial frame 442, a set of half-hinge elements is provided (in FIG. 4A, four half-hinge elements 460 are shown). In some embodiments, the half-hinge elements 460 are formed integrally with the rest of the cranial frame 442. The cranial frame 442 may be designed with 3D CAD software (such as the 3D CAD software sold under the trade name "SOLIDWORKS" by Dassault Systémes [France]) to fit the desired dimensions to maximize the cranial area available for experiments, and constructed preferably out of ultraviolet-cured resin (approximating ABS-plastic when cured) and formed on a 3D printer. The cranial frame 442 of FIG. 4A is provided with an anterior portion 412 that preferably is tapered to closely follow the natural taper of the anterior cranium of the subject (e.g., a rat), and a posterior portion 414 that is wider than the anterior portion 412. The wider posterior portion 414 is believed to provide increased stability of the headmount when fully assembled and installed in the subject relative to any lateral forces the headmount may be subjected to in use in a given experimental protocol. The cranial frame 442 is provided with a lip 416. The lip in the rear portion provides added strength as well as a guide preventing the hinges from being installed incorrectly.

Figure 4B:
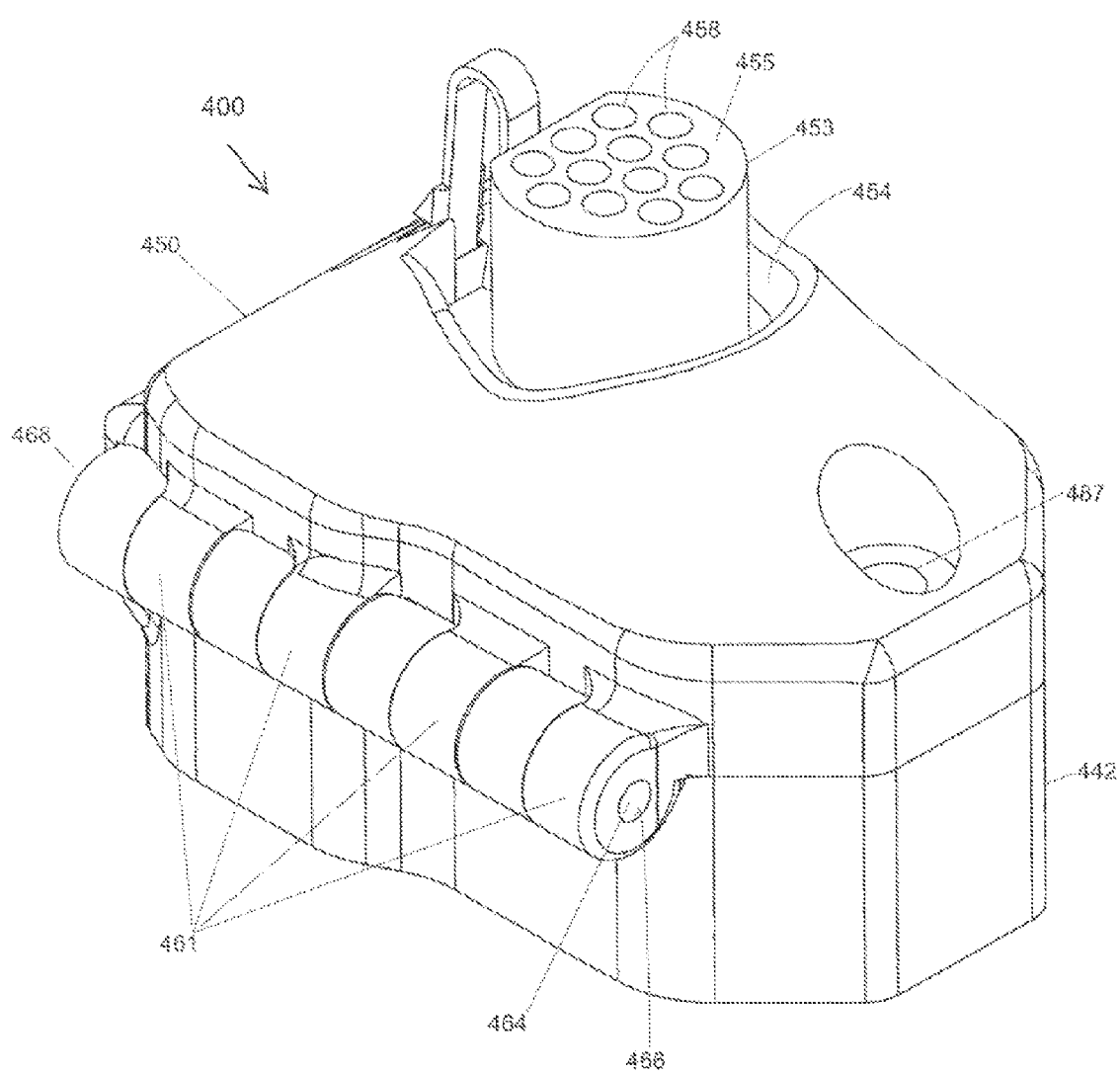
FIG. 4B is a perspective view of a headmount in accordance with an embodiment incorporating the cranial frame of FIG. 4A.

FIG. 4B illustrates a headmount 400 with the cranial frame 442 of FIG. 4A with a headstage 450 associated therewith.

The headstage 450 is provided with a set of headstage half-hinge elements (in FIG. 4B, four half-hinge elements 461 are shown). The headstage half-hinge elements 461 may be formed integrally with the headstage 450 or separately from the headstage and then attached to the headstage by an appropriate means, such as an adhesive. In order to complete the hinge 468, a stout wire or small diameter rod 464 is provided and may be inserted into a central channel 466 formed when the cranial frame half-hinge elements 460 are joined or mated with the corresponding headstage half-hinge elements 461. The stout wire or small diameter rod 464 may provide strength to the structure and will allow the headstage 450 to pivot relative to the cranial frame 442. It will be appreciated that a hinge 468 with the aforedescribed configuration can be disassembled (after any attaching screws are removed) as needed, so that the headstage 450 may be replaced with another headstage 450 (e.g., when a circuit board associated with a headstage 450 is corrupted or nonfunctional) or the headstage 450 can be removed for reuse with another subject. One aperture 487 for receiving an attaching screw for attaching the headstage 450 to the cranial frame 442 is shown in FIG. 4B. FIG. 4B also shows a connector aperture 454 with a latching connector 453 extending therethrough In some embodiments, the latching connector 453 is the male portion of a 12-pin connector commercially available item sold under designation "Micro latching plastic circular-straight" connector available from Omnetics Connector Corporation is used with the headstage 450. Receptacles 458 are provided in a top surface 455 of the latching connector 453. Each receptacle 458 is associated with a pin (e.g., a gold pin) which extends through the latching connector 453 to a bottom surface of the connector (not shown in FIG. 4B). Each pin is associated at the bottom surface with a "mounting lead" which then may be, for example, routed through a through-hole in a printed circuit board and then soldered to a lower surface of the circuit board. The operation of latching connector 453 is described in further detail below.

Figure 4C:
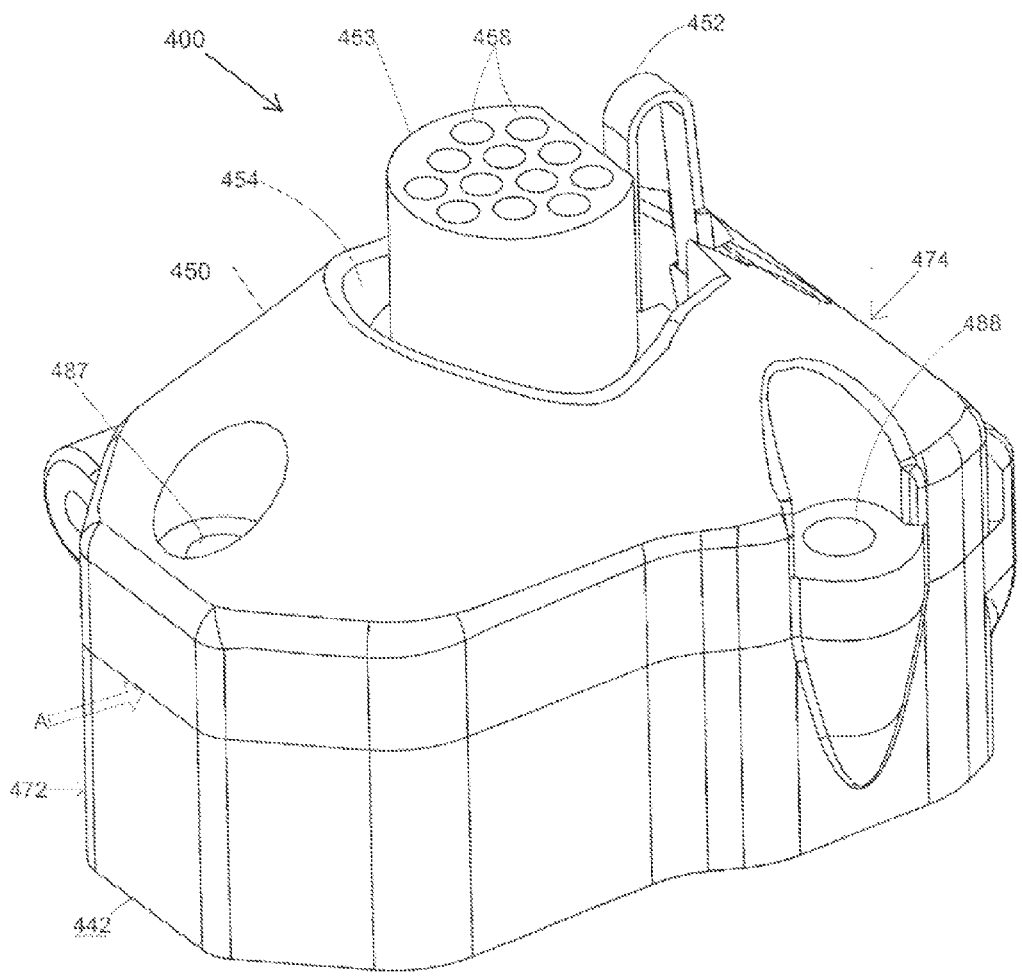
FIG. 4C is an alternate perspective view of the headmount of FIG. 4B.

FIG. 4C is another view of the headmount 400 of FIG. 4B. In some embodiments, as shown in FIG. 4C, the perimeter of the headstage 450 closely matches the perimeter of the cranial frame 442. This aspect is believed to contribute beneficially to the strength of the mating of the two components at the juncture indicated by the arrow A, as well as a moisture-resistant connection. Two apertures for receiving attaching screws are shown in FIG. 4C, one aperture 487 provided in an anterior portion 472 of the headstage 450 and the other aperture 488 towards a posterior portion 474 of the headstage 450. The aperture 487 that is anterior is configured so that it allows an attachment screw (not shown in FIG. 4C) that it receives to pass all the way or almost all the way through the thickness of the headstage 450 (including the material from which the headstage 450 is formed and any circuit board provided integrally with or as a part of the headstage 450) to the frame. The aperture 488 that is posterior is configured so that it allows an attachment screw (not shown in FIG. 4C) that it receives to pass through the material from which the headstage 450 is formed in the posterior portion 474. The connector aperture 454 in the headstage 450 is shown as closely following the exterior dimensions of a male connector that is a latching connector 453 having a latch 452 and provided with receptacles 458 for receiving a mating female connector (not shown in FIG. 4C).

Figure 4D:
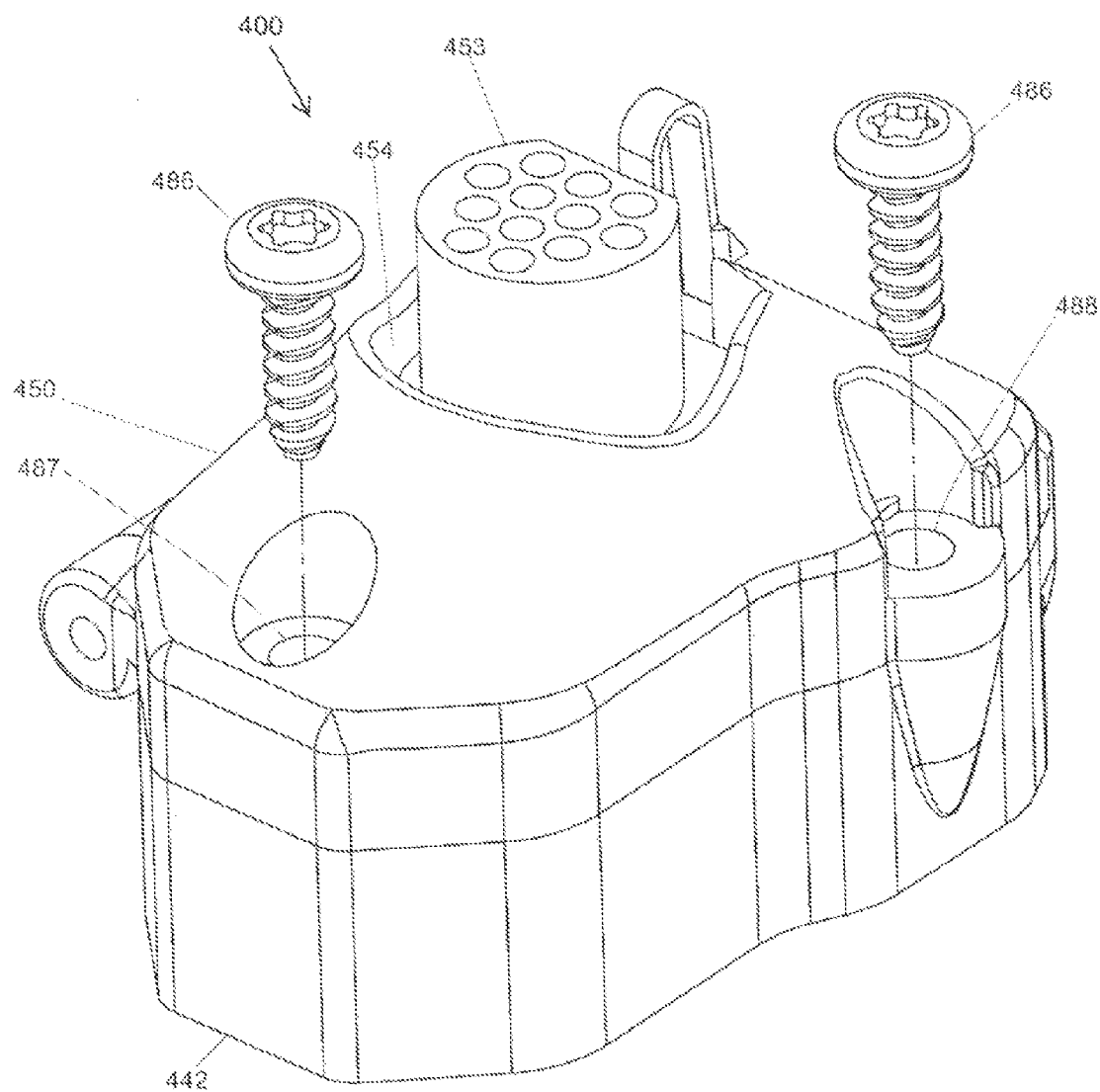
FIG. 4D is an exploded perspective view of the headmount of FIG. 4C illustrating attachment screws.

In FIG. 4D, attachment screws 486 for attaching the headstage 450 to the cranial frame 442 are shown positioned over the apertures 487 and 488. Attachment screws 486 preferably are provided with coarse threading, so that each may securely grip the material of the headstage 450 as a result of the process of mounting the headstage 450 on the cranial frame 442.

Figure 4E:
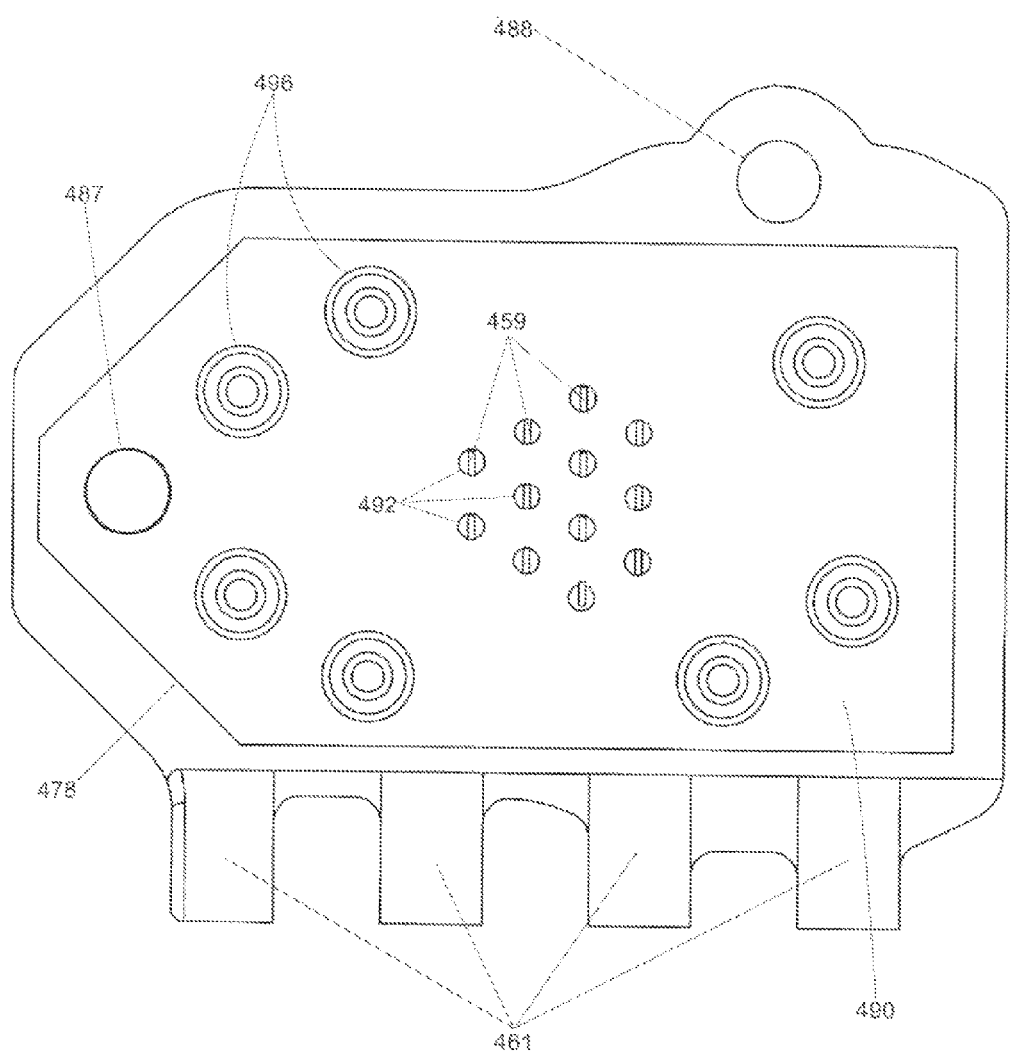
FIG. 4E is a plan view of a lower surface of a headstage of the headmount of FIG. 4B.

FIG. 4E illustrates a lower surface 490 of a printed circuit board 478 which may be used with some embodiments of a headstage 450. The view is of a lower surface 490 of the PCB 478. Apertures 492 through which the mounting leads 459 may be routed are provided in the PCB 478. The distal ends 497 of the mounting leads 459 are shown positioned in the apertures 492 in FIG. 4E. The distal ends 497 may be soldered at the lower surface 490 of the PCB 478. In some embodiments, the PCB 478 is designed to fit within a recessed portion (not shown in FIG. 4E) created in the headstage 450 at the time the headstage 450 is formed. In these embodiments, the PCB 478 will be encased on five sides (e.g., left, right, front, rear, and top) by the headstage 450. Pin receptacles 496 for receiving wires from electrodes implanted in the subject (e.g., screw electrode wires and/or wires from twisted pair bipolar electrodes) also may be provided in the PCB. (In some embodiments, the pin receptacles 496 are an alternative to the pads 396, 394, 398, and 399 described in connection with FIG. 3E). The electrode wires may be attached to the pin receptacles by soldering or other appropriate means on the lower surface 490 of the PCB 478. The PCB 478 further may be provided with conductive traces (not shown in FIG. 4E) to connect the pin receptacles 496 to a corresponding mounting lead of mounting leads 459 so that a signal may be conducted through any system element attached to the latching connector 453 (e.g., a female connector that mates to the latching connector 453).

In some embodiments, the PCB 478 may be mounted so that it is approximately flush with a horizontal plane of the headstage 450 material with the use of a two-part electronics potting epoxy (not shown). This mounting technique serves to securely mate the PCB 478 with the rest of the headstage 450, provides some rigidity to the headstage 450, and aids in keeping moisture out of the interior of the headstage 450. Further, when an electronics epoxy is used, the electronics epoxy may act as a heat sink (e.g., during the course of surgery to install the electrodes and the headmount), when wires associated with the electrodes are soldered. The heat sink aspect is expected to minimize heating of the material from which the headmount is formed (e.g., an ABS-like plastic) and further is expected to absorb a significant amount of the heat generated during soldering, discouraging the electrodes from conducting heat into the subject's tissue. In some embodiments, the same or similar electronics epoxy can be applied to any exposed soldered mounting lead ends 497 on the lower surface 490 of the PCB 478 in order to protect them from moisture and the inadvertent deposition of solder used during the surgery process.

Figure 5A:
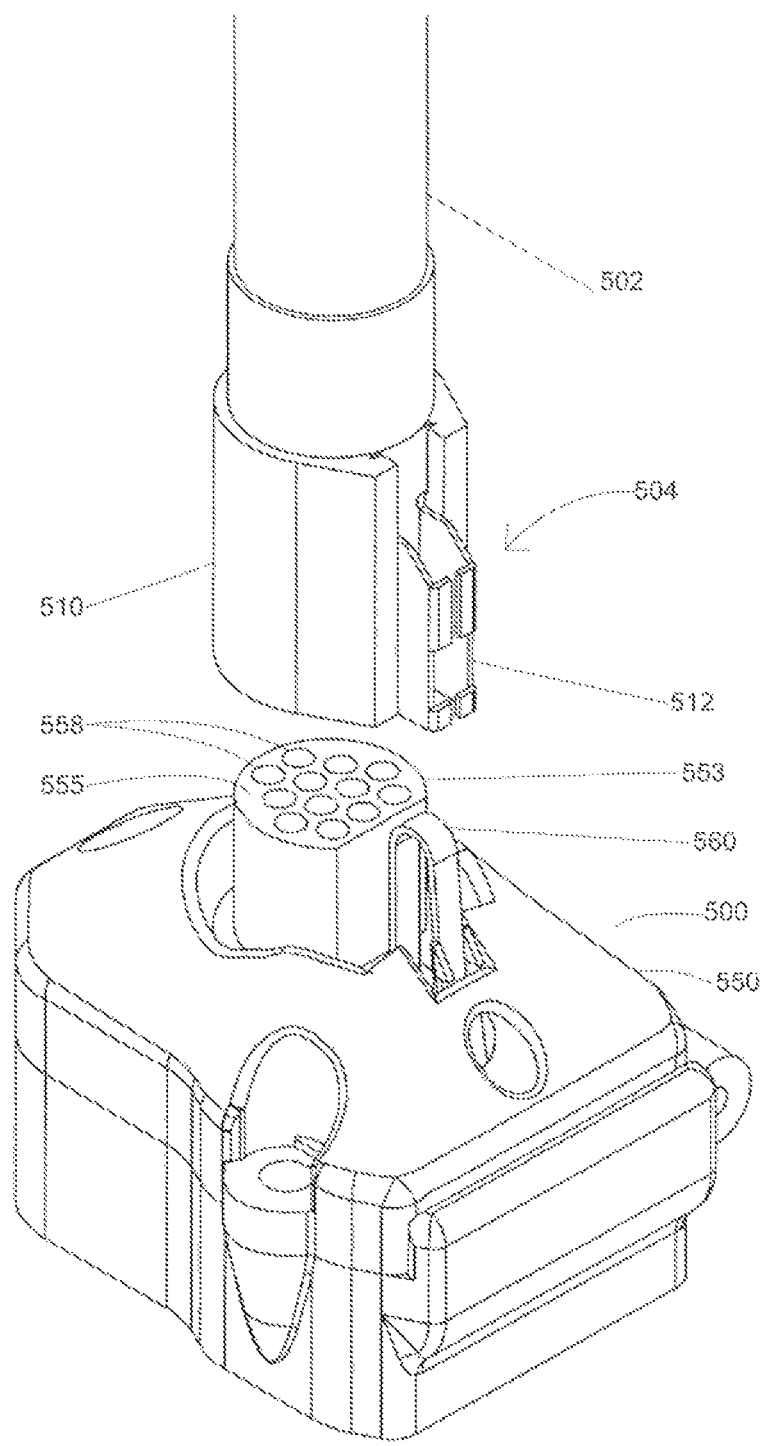
FIG. 5A is an exploded perspective view of a headmount according to an embodiment and a cable with which the headmount may be used.
Figure 5B:
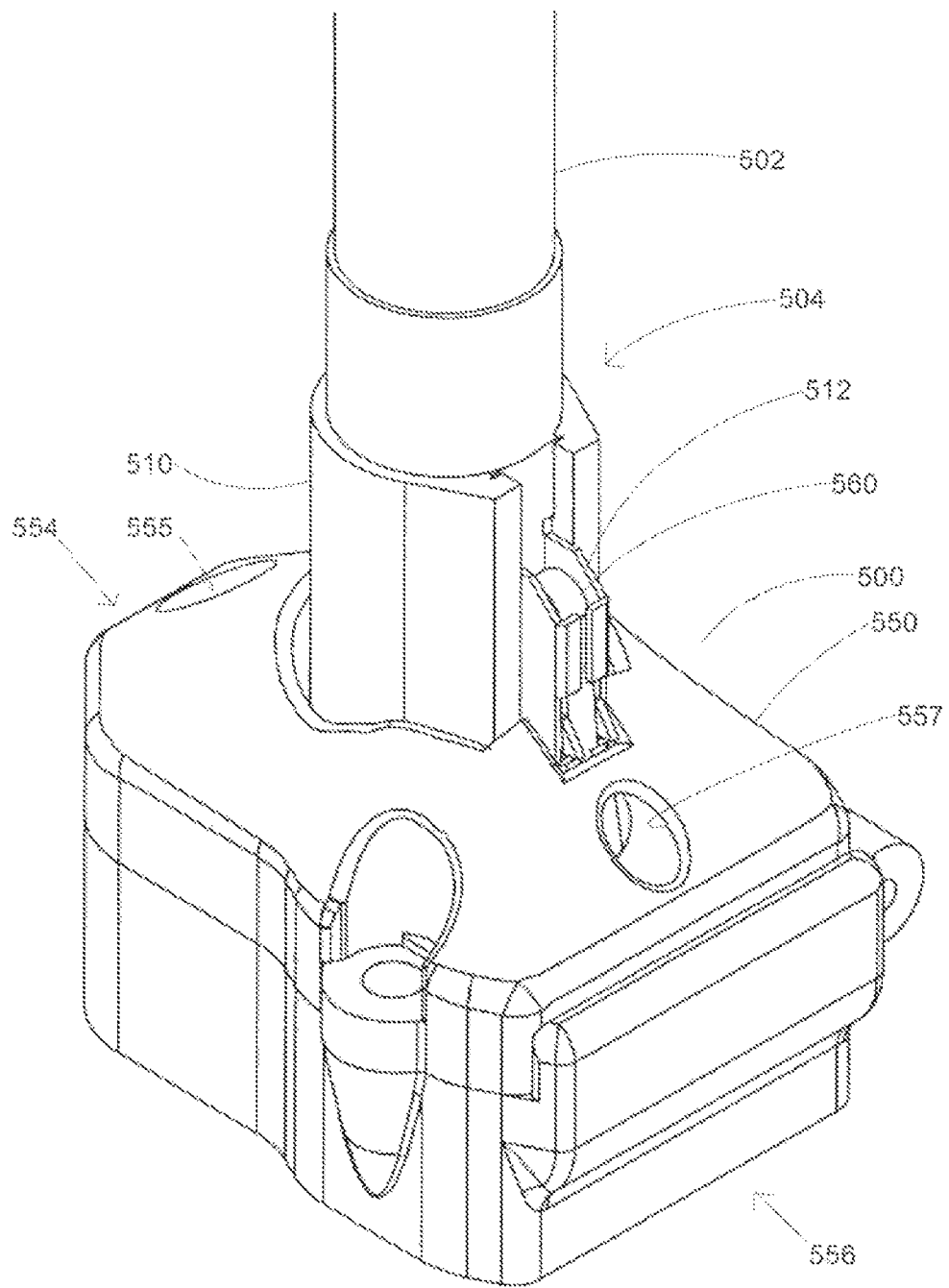
FIG. 5B is a perspective view of the headmount and cable shown in FIG. 5A.

FIGS. 5A-5B illustrate attachment of a cable with a headmount 500 according to some embodiments. A cable 502 is shown with a distal portion 504 and a female connector 510 disposed thereon. The female connector 510 is configured to mate with a male connector 553 on a headstage 550 of the headmount 500. The female connector 510 is provided with a latch-receiving element 512 which is configured to receive a latch 560 associated with the male connector 553. In FIG. 5A, the cable is positioned above the connector 353 that latches and in FIG. 5B, the latch 560 of the connector 353 is shown engaged with the latch-receiving element 512 of the female connector 510. More particularly, when the female connector 510 (such as from a pre-amp cable such as described in connection with FIG. 1 above) is mated to the male connector 553 in the headstage, the latch on the male connector 553 springs out slightly providing a positive lock. Desirably, the headstage 550 encloses a large portion of the male connector 553 in order to minimize the risk of accidental release of the latching mechanism, for example, by reason of the subject's movements. A cut-out 557 may be provided in a posterior portion 556 of the headstage 550. This cut-out 557 may allow a user to access the latch 560 while nevertheless guarding against accidental release of the latch.

In some embodiments, optionally a tool may be provided that a user may insert into the cut-out 557 to depress the latch 560 and thus to cause the latching mechanism (i.e., the latch 560 associated with the [latching] male connector 553 and the latch-receiving element 512 provided on the female connector 510) to disengage so that the female connector 510 can be detached from the male connector 553. In some embodiments, the female connector 510 is a modified version of a female connector available from the Omnetics Connector Corporation. The commercially-available part is modified to include a small section of heat-shrink tubing that abuts the rear of the female connector 510 and encloses a section of woven plastic braid (i.e., the woven plastic braid sold under the name "FLEXO" by TechFlex, Inc.). The woven plastic braid encloses the conductive wires that comprise the connection between the cable 502 (e.g., a pre-amp cable) and the pins of the female connector 510. In some embodiments, the braid and heat-shrink tubing are epoxied to the female connector 510 for strength. The braid is believed to provide strength and strain relief for the wires it encloses and to protect the wires from being damaged (e.g., from being chewed by the subject). The heat shrink tubing is expected to provide additional strength and strain relief between the female connector 510 and the cable 502.

When the cable 502 is connected to the headstage 550, it is securely latched in place with the connector positive lock latching mechanism. In some embodiments, the latch 560 and latch-receiving element provided in the female connector 510 may be formed from a metal. The latching configuration allows a tethered animal to remain securely attached to the tether, which is desirable for long term sensing and stimulus delivery, while also allowing the mechanism to be easily released for handling of the animal. In some connector configurations commonly used with research subjects, the connectors may be provided with plastic threading that is easily stripped or plastic couplers that break. The use of the (latching) male connector 553 in the headstage 550 provides better locking stability due to the strength of the latching mechanism and therefore provides a more consistent and stable connection.

Referring now to FIGS. 6A-6F embodiments of a headmount assembly 600 in accordance with embodiments will now be described. A headmount 602 including a headstage 650 attached by a hinge 660. A flexible braided cable 610 is provided with a proximal end 612 and a distal end 614 and is operably associated with the headmount assembly 600. The flexible braided cable 610 provides connectivity between electrodes implanted in the subject and connected to the headmount 602 and a male connector 653 (which male connector 653 may be connected to other components of an experimental set up, such as a pre-amp cable (not shown in FIG. 6A). The flexible braided cable 610 encloses insulated wires corresponding to the electrodes and the connector pins (not shown) of the male connector 653. The flexible braided cable 610 provides strength, protection, and strain relief for the wires. The insulated wires comprising the flexible braided cable 610 are soldered at the distal end 614 into through-hole vias in a PCB (not shown) in the headstage 650.

The flexible braided cable 610 extends into the headstage 650 through a generally round or elliptically-shaped channel in a posterior portion of the headstage 650. The flexible braided cable 610 and the wires therein are epoxied to a PCB inside the headstage 650, thus securely mounting the flexible braided cable 610 to the headstage 650. In some embodiments, silicone may be applied so that it is deposited between the flexible braided cable 610 and a cylindrical inner surface of the channel in the headstage and extends to slightly beyond the opening of the channel, thus providing further strain relief for the flexible braided cable.

In some embodiments, the flexible braided cable 610 is attached to the headstage 650 so that the flexible braided cable 610 extends away from the headmount 602 at an angle that is approximately 45 degrees from a horizontal plane as the flexible braided cable 610 exits the posterior portion 652 of the headstage 650. The angled configuration allows any forces that are exerted on the headstage 650 by components to which the subject is tethered (e.g., a pre-amp cable) to be deflected along an anterior-posterior axis of the headmount 602, which has good contact with the subject's cranium and is thus a stronger axis than the left-right-axis and will resist spontaneous detachment of the headmount 602 from the subject. Additionally, the approximately 45-degree angle allows the headmount 602 to have a swept-back profile, providing a lower profile overall, for example, lower profile than the embodiment of FIG. 4A-4E, interfering less with the subject's movement, as well as keeping the flexible braided cable 610 in a direction less accessible to the animal (e.g., behind its head) than might be, for example, a food tray or a water bottle provided in the subject's enclosure and also likely will prevent the animal from being able to chew on the flexible braided cable 610. The angled configuration may also prevent the flexible braided cable 610 when connected to other components of an experimental set up, such as a pre-amp cable (not shown in FIG. 6A), from snagging on other components of the experimental set-up (like a food tray or water bottle).

In some embodiments, the male connector 653 provided at the proximal end 612 of the flexible braided cable 610 is a latching (male) 12-pin connector. The (latching) male connector 653 may be configured to mate with a female connector provided on another cable, such as the pre-amp cable 1008 described in connection with FIG. 1, above.

Figure 6A:
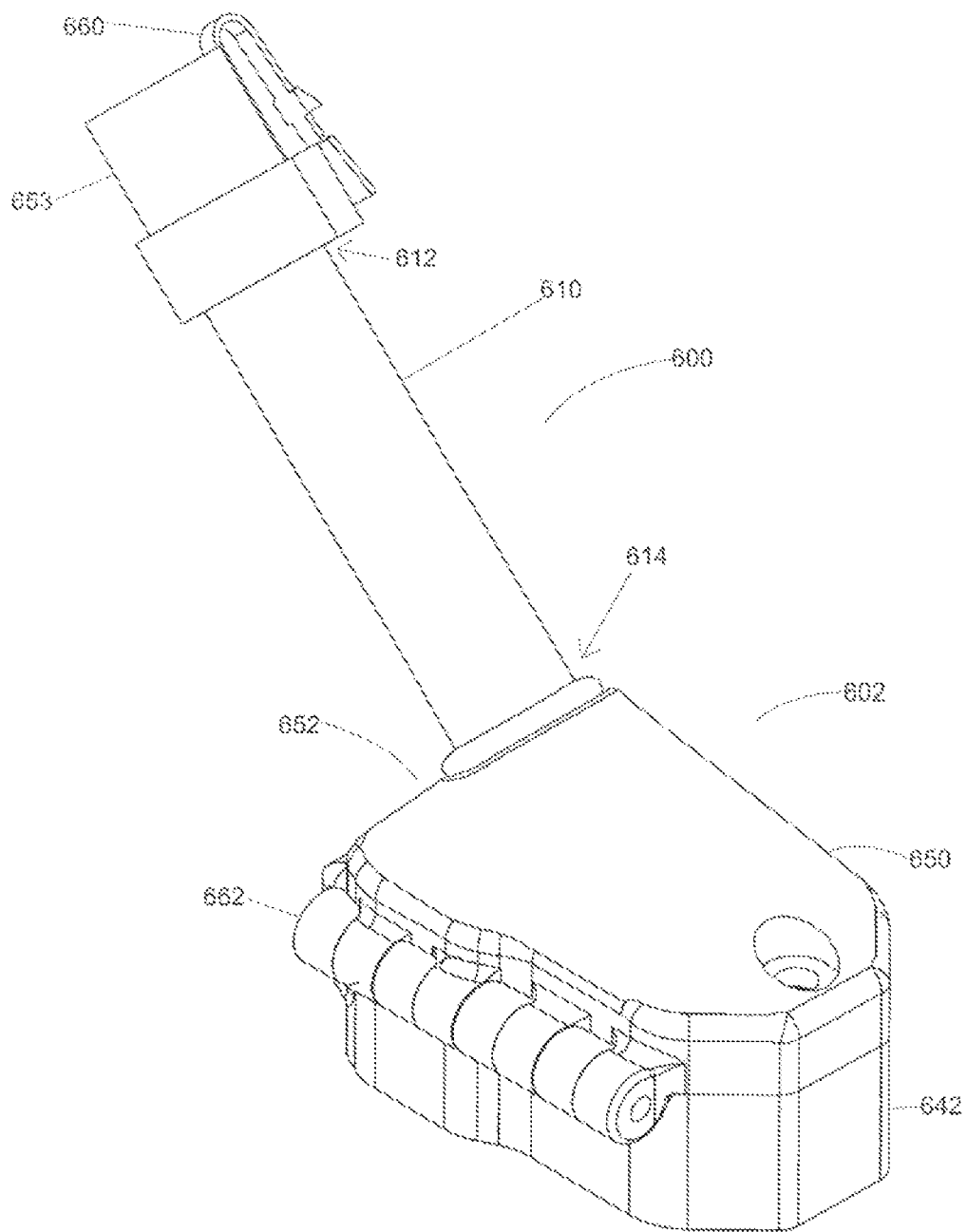
FIG. 6A is a perspective view of a headmount assembly in accordance with an embodiment.
Figure 6B:
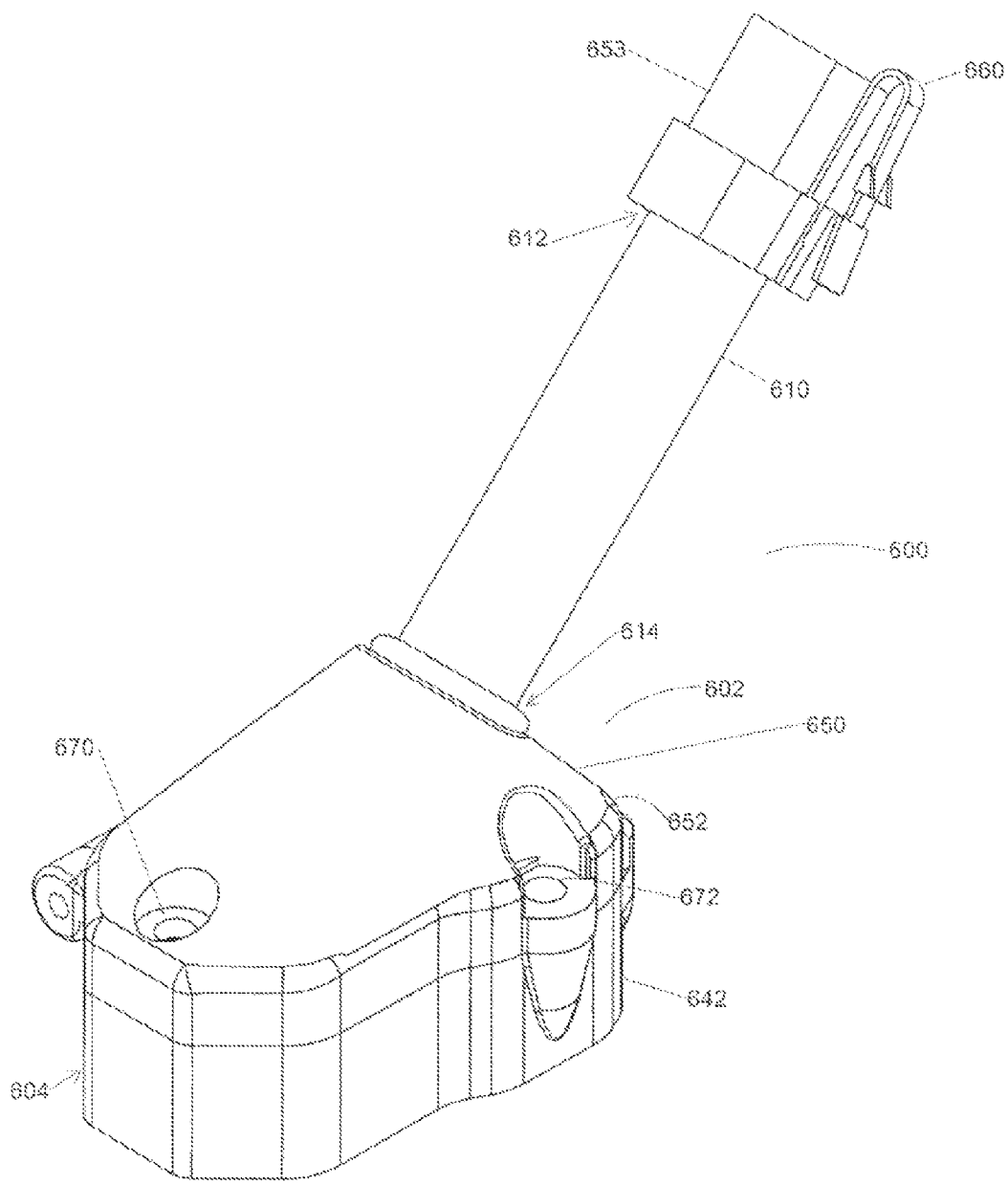
FIG. 6B is an alternate perspective view of the headmount assembly of FIG. 6A.

FIG. 6B is alternative view of the headmount assembly 600 of FIG. 6A. Apertures 670, 671 for receiving an attachment element, such as an attachment screw, are shown, respectively, in an anterior portion 604 of the headmount 602 and in a posterior portion 652 of the headstage 650.

Figure 6C:
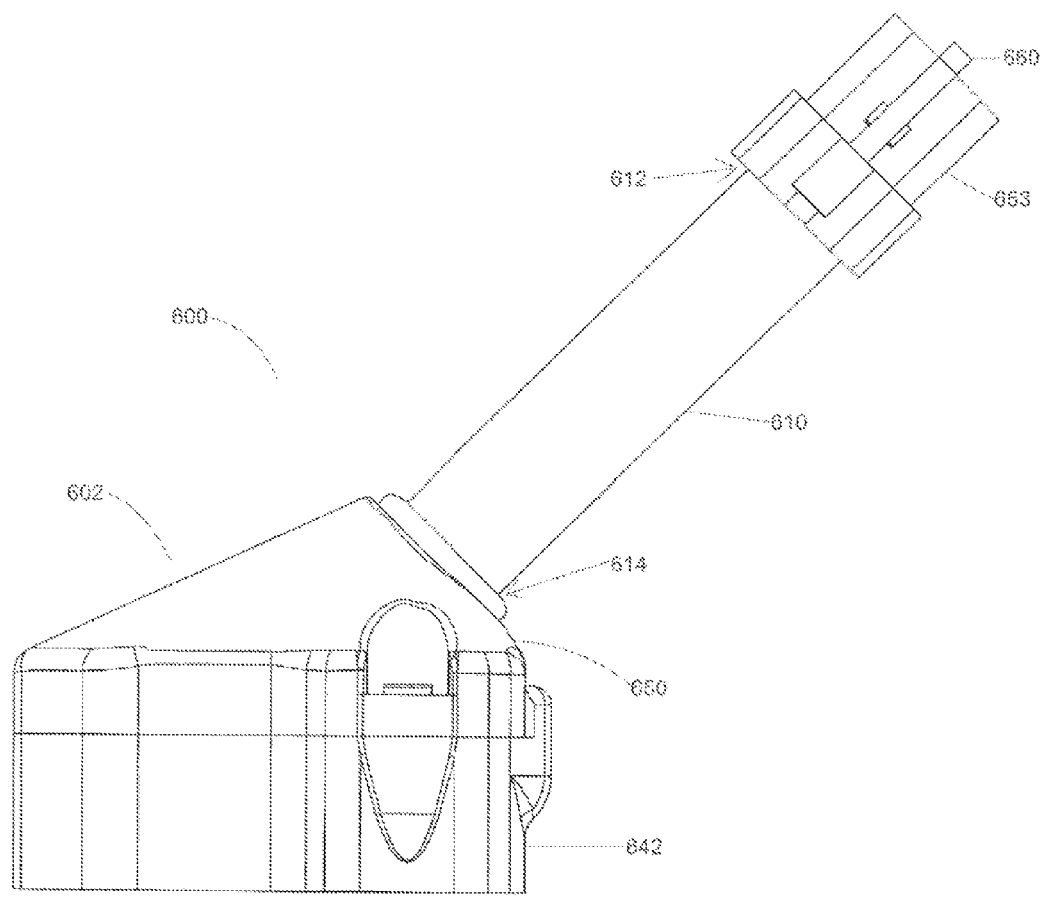
FIG. 6C is an elevational view of the headmount assembly of FIG. 6A.

FIG. 6C is a side view of the headmount assembly 600 of FIG. 6A illustrating the swept back angle between the headmount 602 and the flexible braided cable 610. It may be appreciated that the angle of exit of the flexible braided cable 610 from the headstage 650 deflects forces applied to the flexible braided cable 610 and headstage 650 to a vertical forward/backward direction rather than a left-to-right torque force that may risk detaching the headmount 602 from the subject. In any tethered system such as the systems described herein in which the headmount assembly 600 may be used, prospective loss of the headmount is an issue to be concerned with, especially when using a pre-amp cable that is large or heavy. Multiple features of the headmount assembly 600 contribute to better distribution of any applied forces and better tolerance of the set up by the animal as compared with conventional configurations, such as the lower profile of the headmount 602 relative to the skull, the flexible nature of the flexible braided cable 610 (as compared to a more rigid connector mounted directly on a headstage), the angle of exit, and the strain relief measures (e.g., silicone, flexibility of the braid).

Figure 6D:
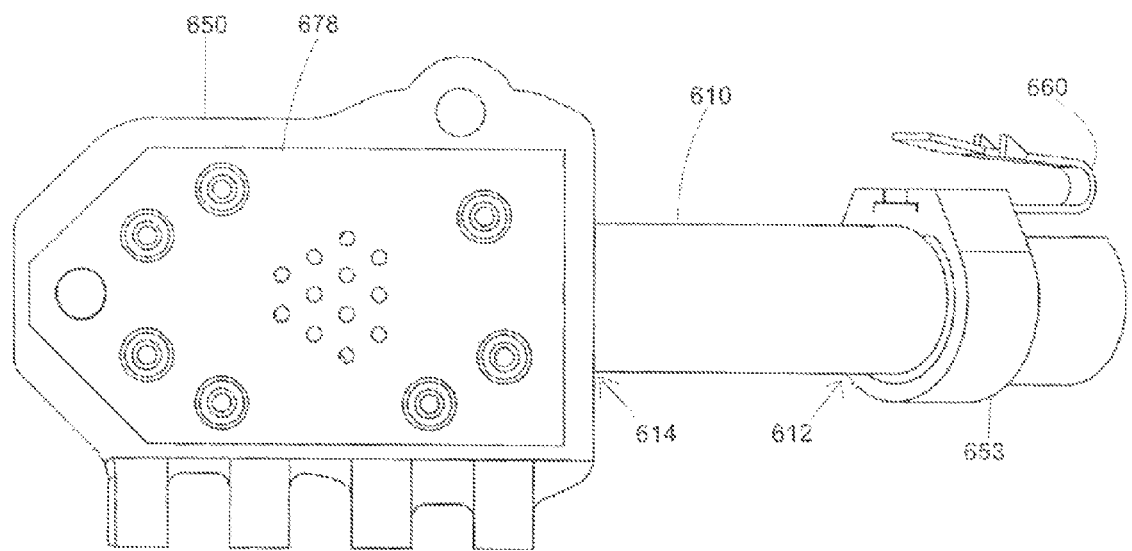
FIG. 6D is a bottom plan view of the interior of the headmount component of the headmount assembly of FIG. 6A.

FIG. 6D is a bottom plan view of headstage 650 in which a printed circuit board 678 has been embedded. The distal end 614 of the flexible braided cable 610 extends from the headstage 650 to a (latching) male connector 653 at the proximal end 612.

Figure 6E:
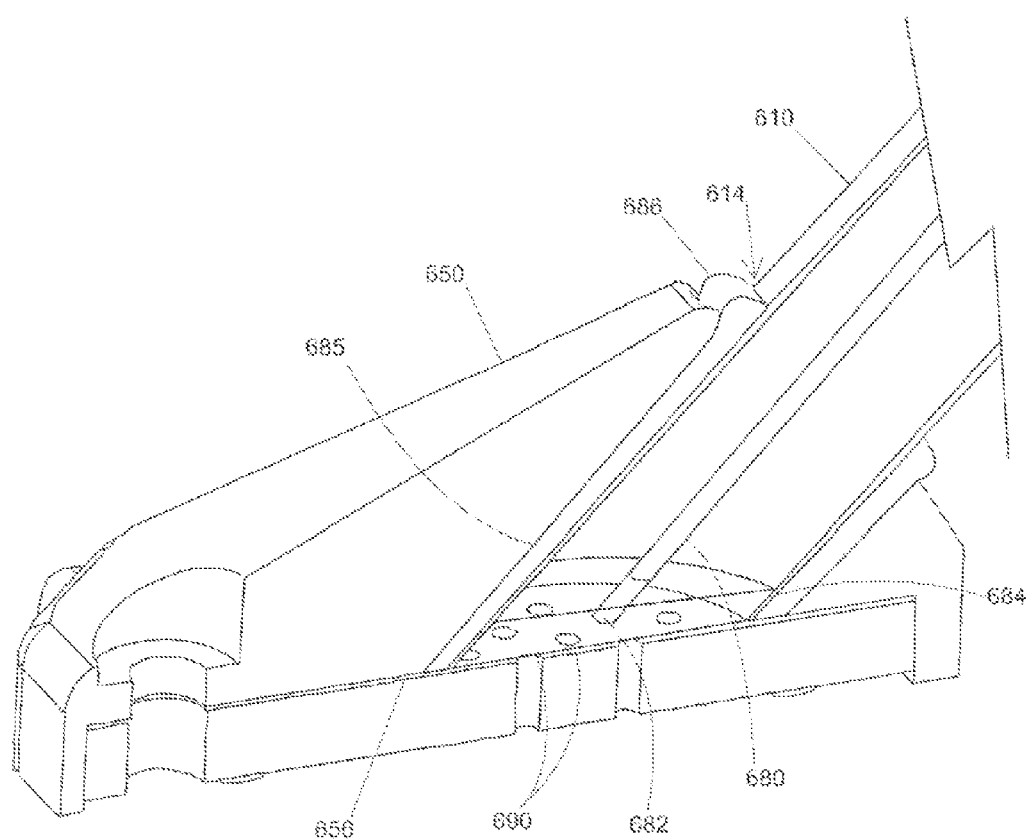
FIG. 6E is a cross-sectional view of the headmount assembly of FIG. 6A.

FIG. 6E is a cross-section of a portion of the headmount assembly 600 at the location at which the distal end 614 of the flexible braided cable 610 is joined to the headstage 650. One conductive wire 680 is shown extending through the cable from a location inside the headstage 650.

To manufacture the headmount assembly 600, the flexible braided cable 610 is passed through a cylindrical channel in the headstage 650. The insulated wires in the flexible braided cable 610 may be Teflon-coated wires (e.g., coated with PTFE) and the flexible braided cable 610 may be commercially available from, for example, the Omnetics Connector Corporation. In some embodiments, to attach the flexible braided cable 610 to the headstage 650, the insulation of the distal ends 682 of the wire(s) 680 contained within the flexible braided cable 610 is stripped away and then the individual wire(s) 680 is placed in through-holes 690 provided in the PCB 678 and soldered into place on the lower surface of the PCB 678. After all of the wires are soldered into place, they are epoxied to the PCB 678 and the flexible braided cable 610 is then epoxied to the PCB 678. A recess in the interior of the headstage 650 (that is sized to accommodate the PCB 678) is covered with a layer of epoxy 656 and the PCB 678 is then secured in the headstage 650. This manner of attachment of the PCB 678 in the headstage 650 contributes to the overall strength of the headstage 650 and affords some heat sinking capacity. Using a syringe or other appropriate instrument, silicone 686 that is uncured is deposited in the space between a channel 685 provided in the headstage 650 and the flexible braided cable 610. The silicone may be characterized by a low to medium durometer so that it is relatively resilient and springy. After the silicone 686 is cured, it serves to provide additional strain relief and to seal the headstage 650 from the environment external to the subject to protect the interior, for example, from moisture.

Figure 6F:
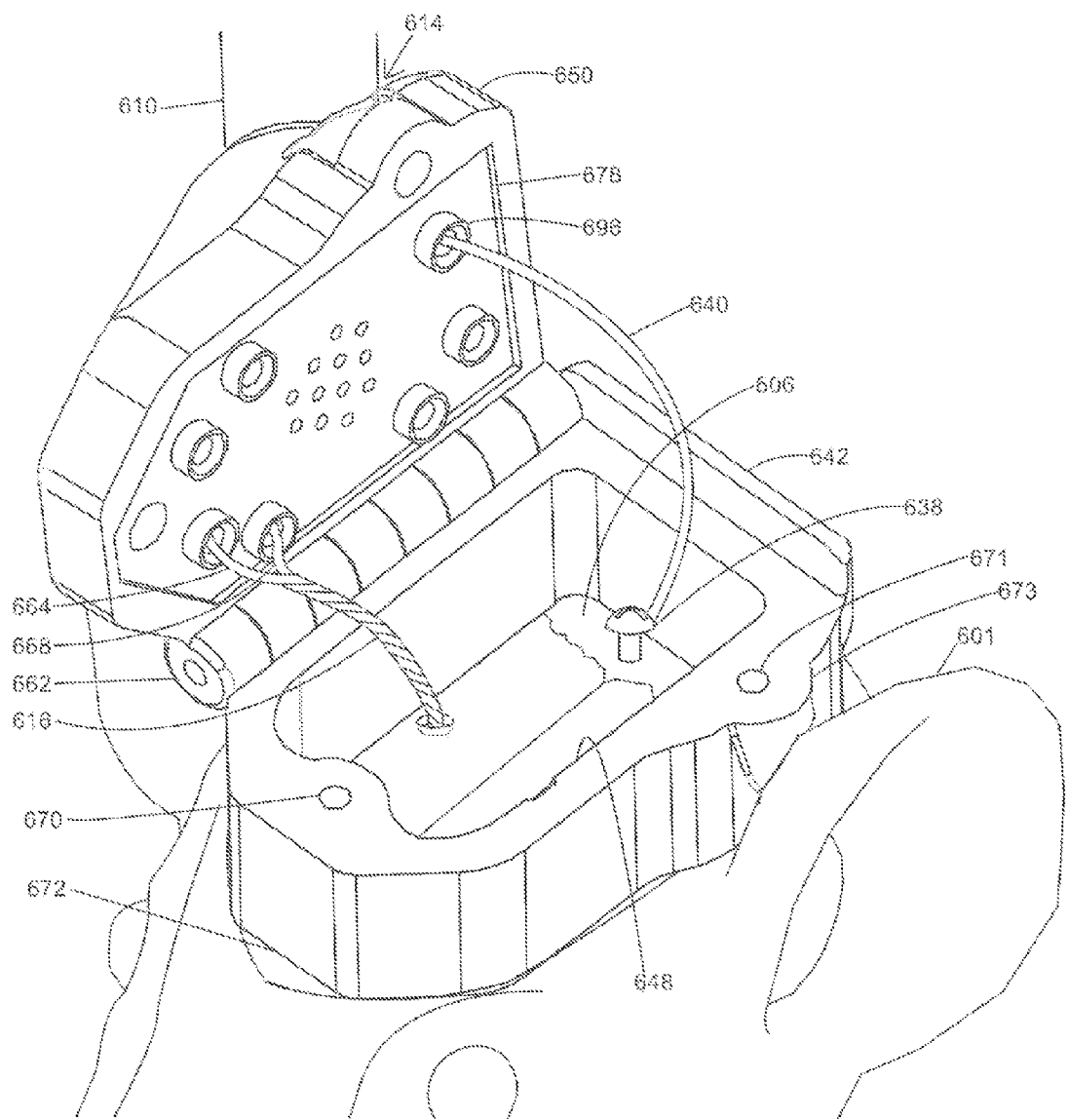
FIG. 6F is a perspective view of the headmount assembly of FIG. 6A in an open configuration.

FIG. 6F shows a fully implanted (in a subject 601) and fully assembled headmount assembly 600 with the headstage 650 pivoted up and away from the cranial frame 642 to expose the interior of the headmount assembly 600 including a PCB 678 and frame aperture 648. A wire 640 extends from a screw electrode 638 and is soldered into place in a pin receptacle 696 in the PCB 678, and is therefore electrically routed through the PCB 678 in the headstage 650 for connection to the flexible braided cable 610 (e.g., to allow signals to be sensed from the screw electrode). A twisted pair bipolar electrode 616 extends from a point in the subject's brain to the PCB 678. The proximal portions 664 and 668 of the primary and secondary wires of the twisted pair bipolar electrode are soldered into place in other pin receptacles 696 in the PCB 678 therefore electrically routed through apertures in the PCB 678 for connection to the flexible braided cable 610 (e.g., to allow sensing from the subject or to allow delivery of stimulation to the subject). Apertures 670, 671 for receiving attachment screws are provided in an anterior portion 672 and posterior portion 673, respectively, of the cranial frame 642.

In a method according to an embodiment, after the subject's cranium is exposed and cleaned during surgery, a plurality of screw electrodes (a stainless steel screw with a wire electrically attached) and bipolar twisted pair microelectrodes (alternatively, other types of physiological sensors may be used) may be implanted using a stereotaxic apparatus. Once positioned, a standard procedure is to fix the electrodes in place at the junction of the electrode with the skull using a small amount of dental cement that is allowed to cure (not shown). Following this, the assembled headstage 650 and cranial frame 642 (with the headstage 650 open at approximately a 90 degree angle) are placed over the electrodes such that the aperture of the frame aperture 648 encloses all electrodes. The electrode wires are pulled up through the frame aperture 648 of the cranial frame 642. The cranial frame 642 is then fixed in place by applying a small amount of dental cement (not shown) to the lower, interior perimeter defined by the frame aperture 648 for the cranium, where the cranial frame 642 meets the skull surface 606. Additional cement may be added to anchor the frame to the implanted electrodes. Once cured, this cement holds the frame in place allowing additional manipulation without the need to manually steady any components; the friction afforded by the hinge 660 keeps the headstage 650 open and approximately vertical which greatly eases the process of soldering the electrode wires in place and allowing the surgeon to use both hands to do so. This shortens the time necessary to perform such surgeries by limiting the number of repeated applications of dental cement that are required and by eliminating the tasks of crimping wire, twisting wire, or applying silver epoxy during surgery. Minimal mixing and drying time is required for the dental cement and the actual electrical connections to the electrodes can be made with the very brief application of solder and a soldering iron. This also serves to provide a superior electrical conduction of biological signals than can be accomplished with the comparably more noise-prone conventional methods.

Figure 7A:
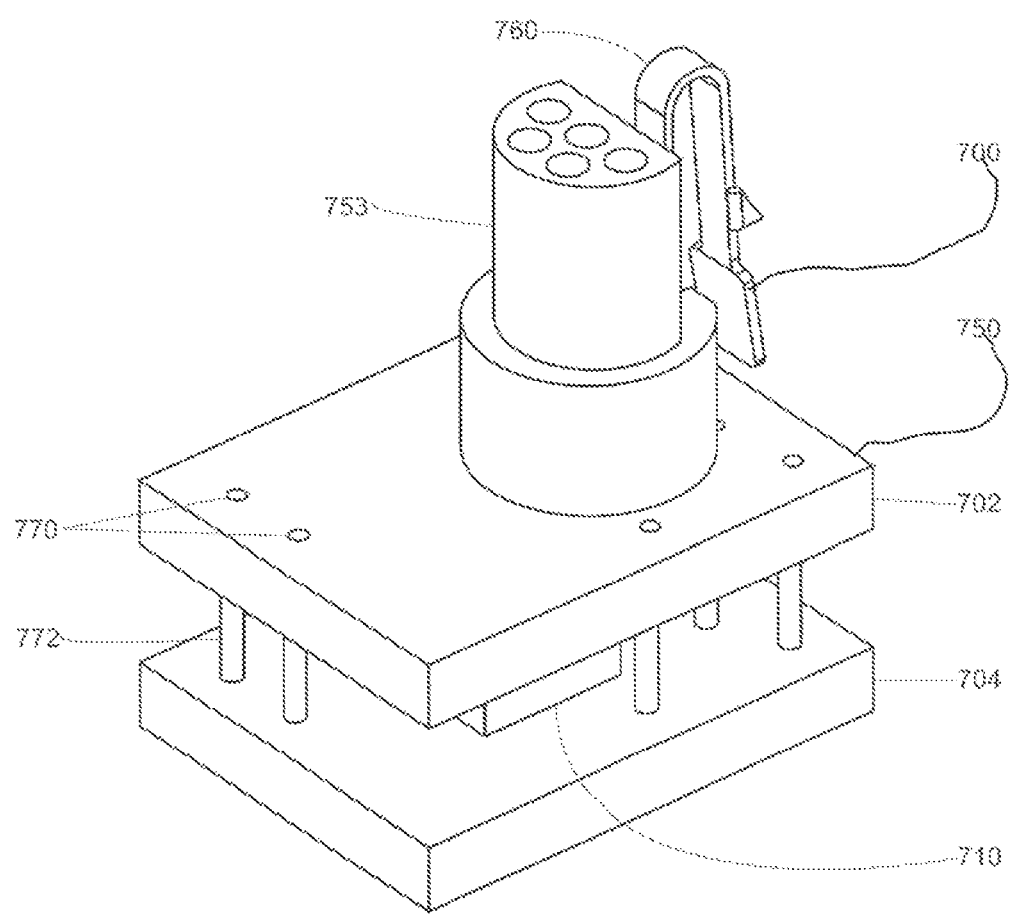
FIG. 7A is a perspective view of a portion of a headstage of a headmount in accordance with an embodiment.
Figure 7B:
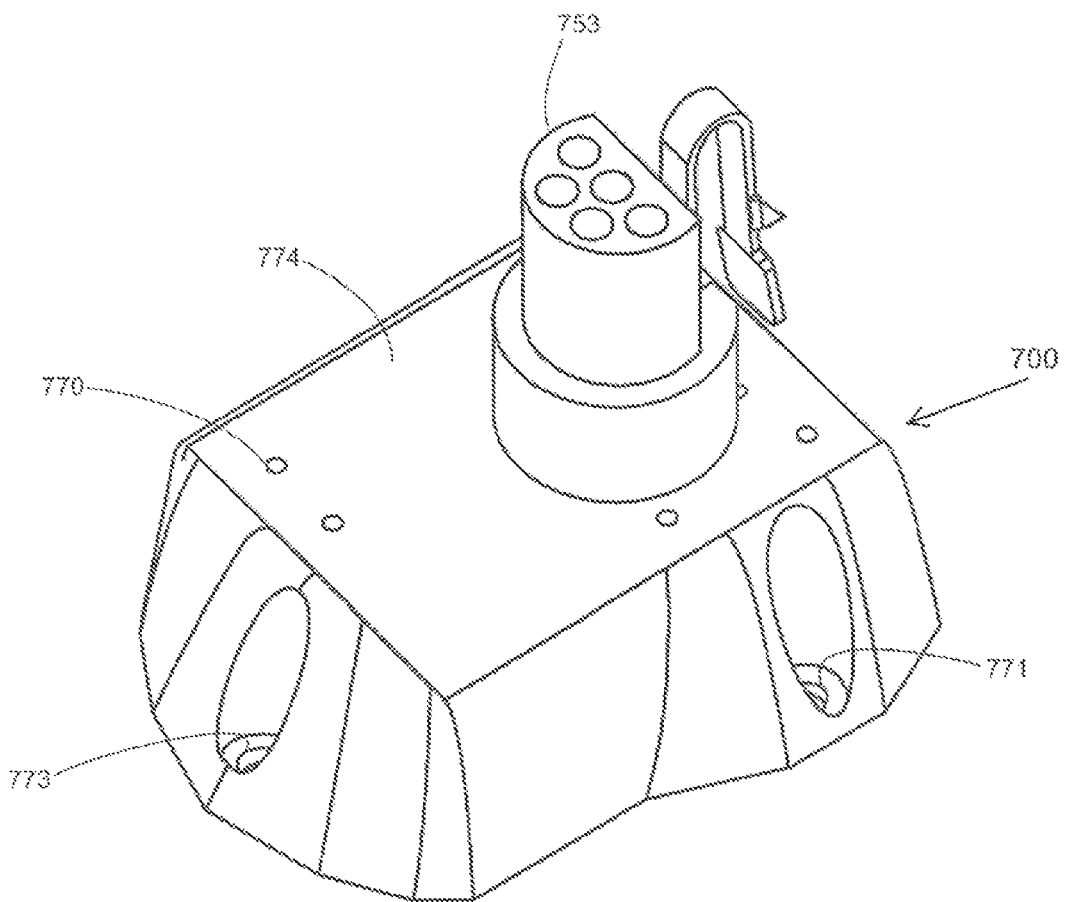
FIG. 7B is an alternate perspective view of a headstage including the portion of FIG. 7A.
Figure 7C:
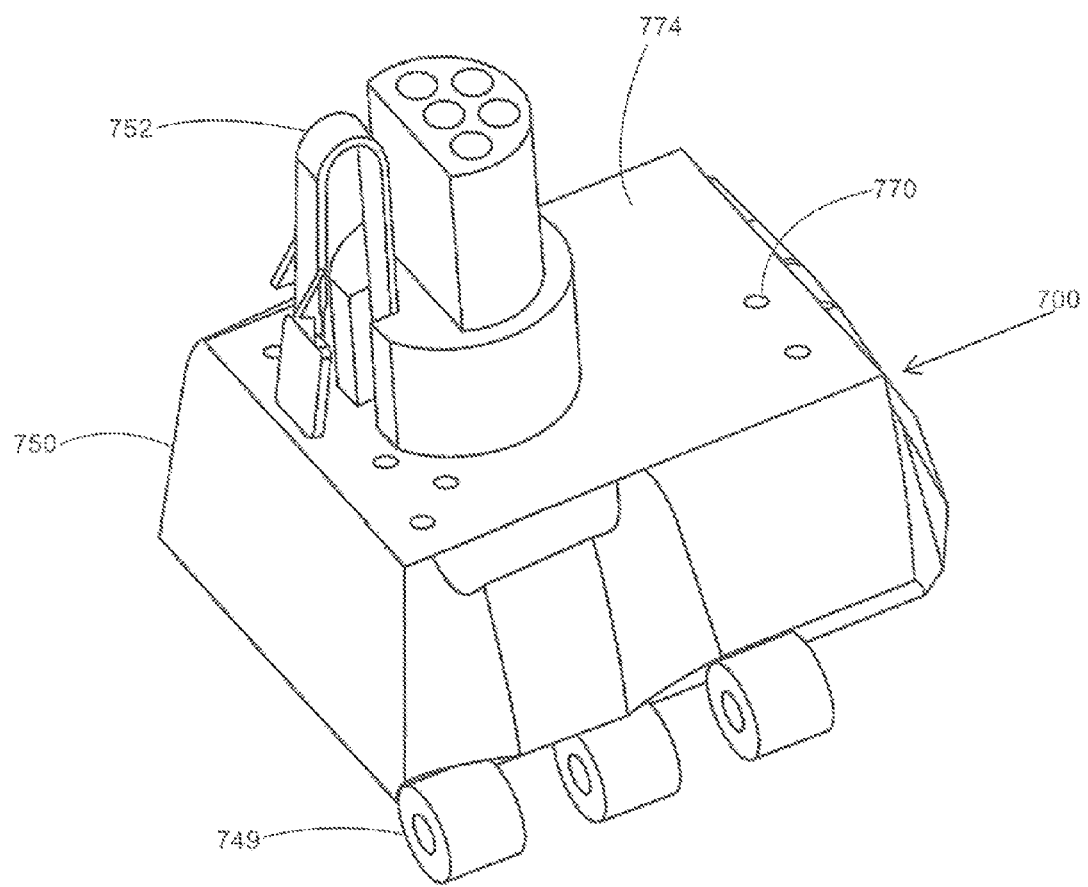
FIG. 7C is a further perspective view of the headstage of FIG. 7B including half-hinge elements.
Figure 7D:
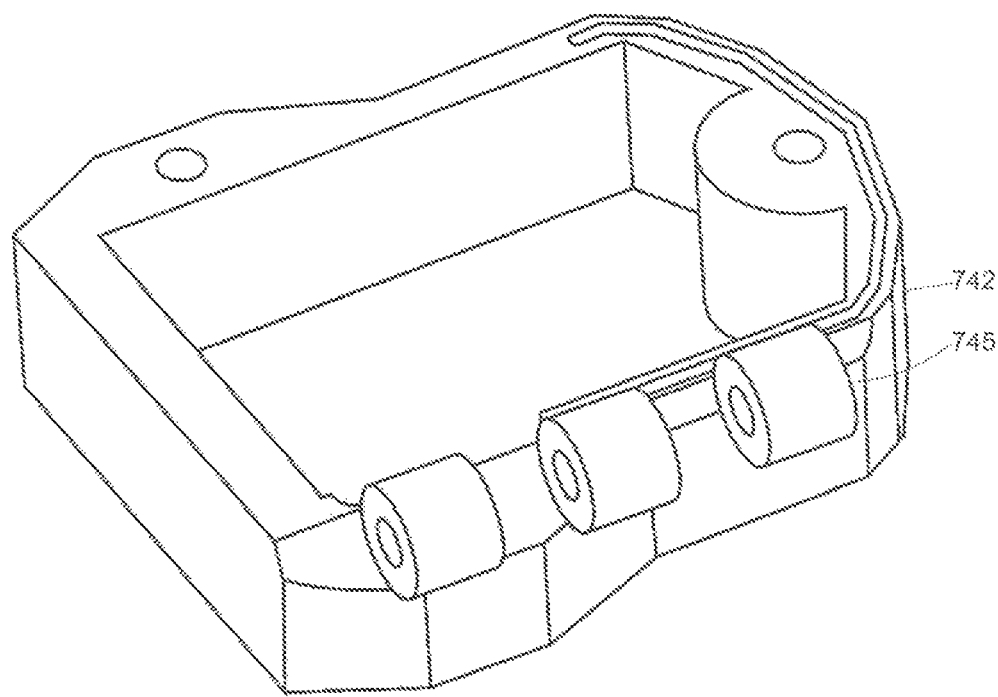
FIG. 7D is a perspective view of a cranial frame that may be used with the headstage of FIG. 7B.

Referring now to FIG. 7A, still other embodiments of a headmount 700 may be realized. Varying configurations of components and circuit boards may be used. In FIG. 7A, a headstage 750 is provided with a first printed circuit board 702 stacked on top of a second printed circuit board 704 in a vertical configuration. Through-holes 770 may be provided that extend all the way through both of the PCBs 702, 704. Wires 772 may be provided in the through-holes 770 and attached to the PCBs by appropriate means, such as by soldering. In addition to providing connectivity between the PCBs 702 704, the wires 772 may provide structural support in spacing the two PCBs apart from each other. Using more than one circuit board may increase the circuit capacity of headmount 700 for use in particular sensing applications, such as when voltammetric sensing (e.g., measurement of neurotransmitter levels) is desired. For example, voltammetric sensing may require the use of amplification circuitry located as close to the subject's brain as possible due to the minute signals being detected. In this case, the limited size of a single circuit board may preclude the presence of sufficient components to achieve the appropriate voltammetric sensing. Addition of a second circuit board allows components to be mounted onto the top and bottom of both circuit boards, effectively doubling the available circuit board area for the inclusion of these important components. Depending on the modality of sensing, a headmount 700 may be configured to include other components 710 (mounted to a printed circuit board, otherwise situated in the interior of a headstage, or otherwise affixed to or extending from a headstage). Examples of these additional components may include a battery, miniaturized pre-amplifiers (e.g., for boosting very small signals) and/or other transducers/transmitters. Alternative mounting platforms for components used in sensing may also be used with beneficial effect with a headmount according to embodiments, e.g., platforms well-suited for various fragile, sensitive, or otherwise specially implanted sensors (e.g., a carbon fiber electrode, photodiodes, optical fibers, etc.). As will be appreciated, headmount assemblies including a flexible braided cable as described above in connection with FIGS. 6A-6F may also be used for different sensing modalities, different forms of stimulation (e.g., other than electrical) or with different mounting platforms.

Figure 7E:
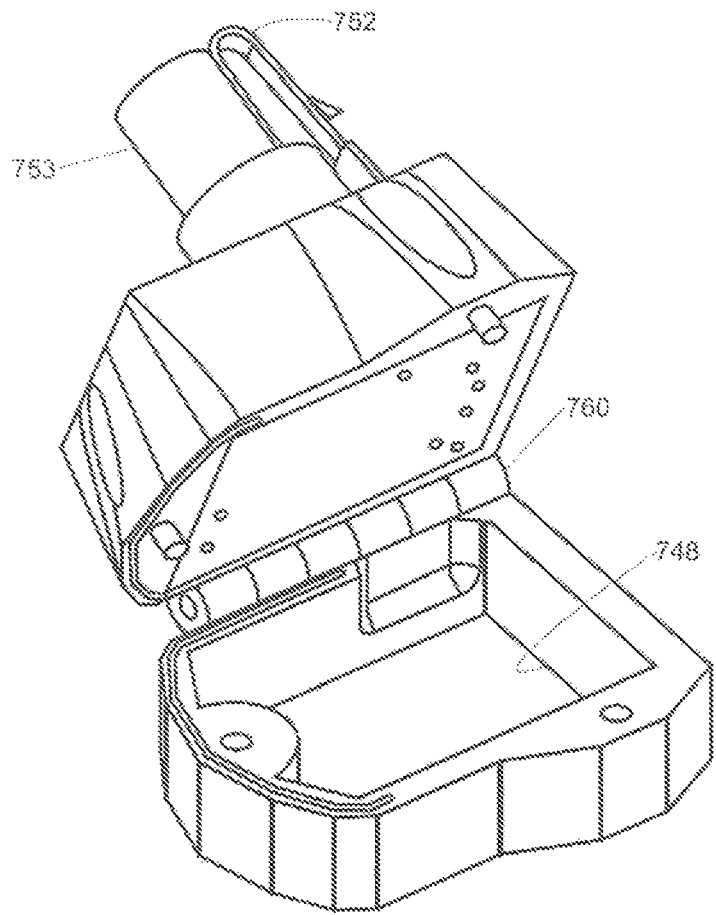
FIG. 7E is a perspective view of a headmount according to an embodiment that incorporates the headstage of FIGS. 7A-7C and the cranial frame of FIG. 7D.
Figure 7F:
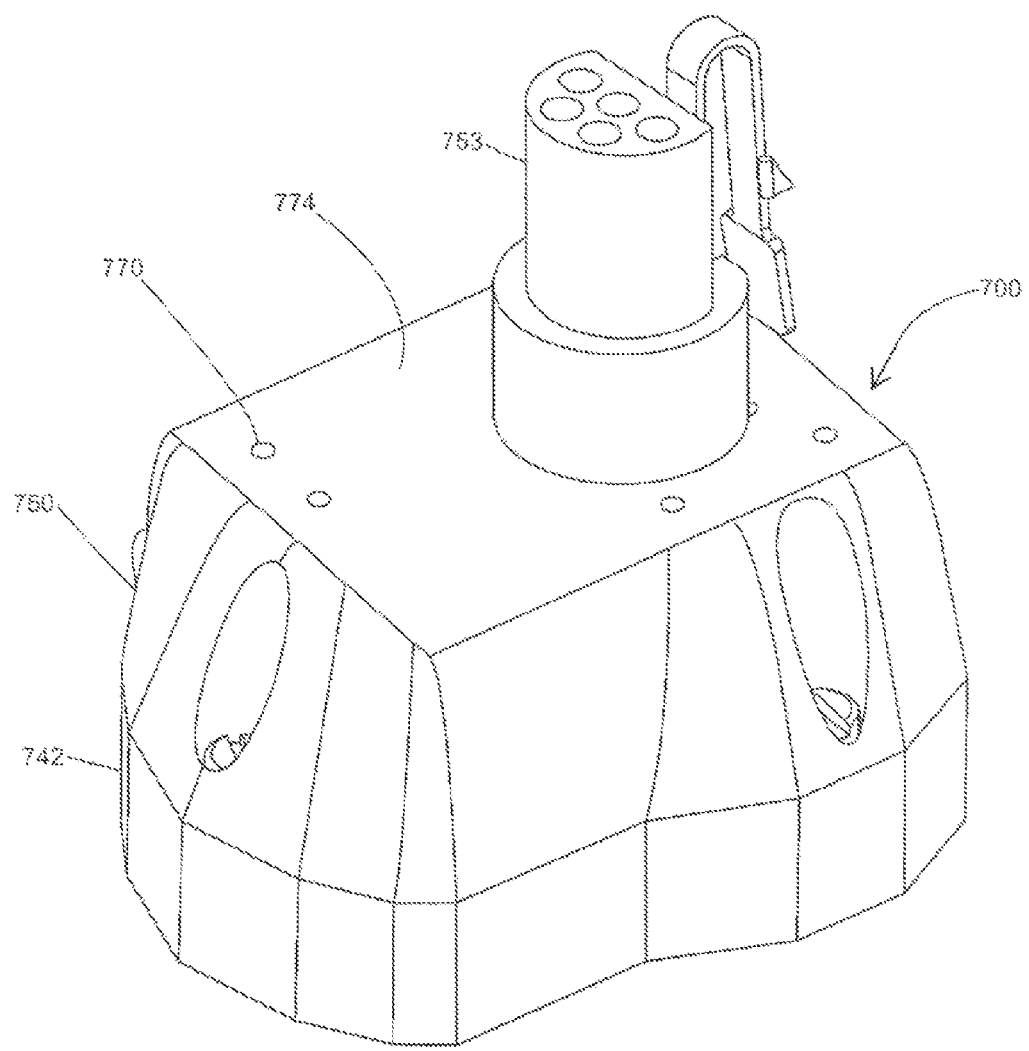

FIGS. 7B-7F illustrate various configurations of a headmount 700 that includes at least two printed circuit boards stacked one on top of the other The through-holes 770 are visible in a top surface 774 of the headmount 700. The embodiments of FIGS. 7B-7F may include a latching connector 753 and associated latch 752, apertures 771, 773 for receiving attachment screws (FIG. 78), half-hinge elements 749 provided on a headstage 750 (FIG. 7C), half-hinge elements 745 provided on a cranial frame 742, a hinge 760 allowing a headstage to be rotated up and away from a cranial frame 742 to allow access to the interior of the headstage 750 and/or to manipulate items in the space defined by the cranial frame aperture 748 (FIG. 7E). It will be appreciated that when the headstage itself or the area interior of the headstage is used for more components or circuit boards than in other embodiments, the overall profile of the headmount 700 may be higher than that of other embodiments, such as those described in connection with FIGS. 4A-4E, FIGS. 5A-5B, and FIGS. 6A-6F. An embodiment of a headmount 700 with a higher profile is illustrated in FIG. 7F.

Based on all of the foregoing, it should be appreciated that a headmount and/or headmount assembly in accordance with embodiments may result in a significant reduction in the cost per day to maintain a subject or subjects in an experiment. The headmount and headmount assembly have features that allow rapid and reliable production of units (e.g., with the 3-D printer and improved PCB design) and the ability to use portions of a unit with more than one subject (e.g., the headstage).

With reference again to FIG. 1, in some embodiments the interface box 1060 generates one or more stimulation triggers 1070 that in turn are passed from the stimulator output generator 1080 as digital triggers 1084 to the stimulation control board 1086. In a default state, i.e. when a digital trigger 1084 is LOW, a corresponding reed relay (not shown) remains open in the stimulation control board 1086 and therefore isolates the stimulation lines for that channel from conducting electrical noise (or stimulation) into the electrical swivel 1010 and thus the pre-amplifier 1008. Additionally, an N-FET (not shown) associated with the same channel is used to, in a default state, pull the pre-amplifier's (also known as "pre-amp") control signals 1030 to ground (i.e., a digital LOW), which in turn keeps the pre-amp cable 1008 in "sense" mode, in which it acquires EEG.

Figure 8A:
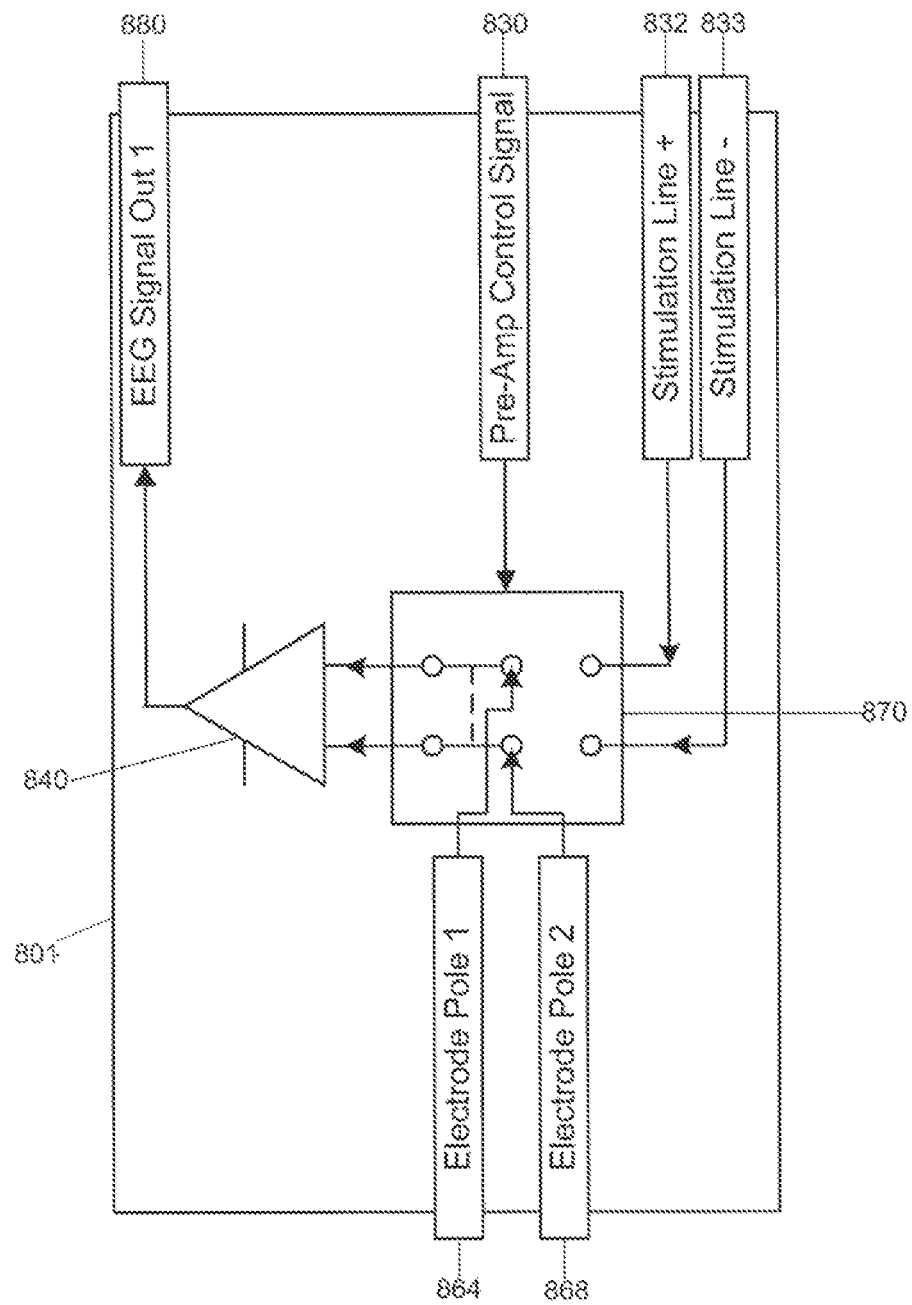
FIG. 8A is a block diagram of a circuit used with a cable in a system in accordance with an embodiment.

Referring now to the simplified schematic presented in FIG. 8A, the pre-amplifier 801, contains a differential amplifier 840. When in "sense" mode, i.e., when the pre-amplifier control signal 830 is digital LOW, the poles of the corresponding bipolar electrodes, a first electrode pole 864 ("Electrode Pole 1") and a second electrode pole 868 ("Electrode Pole 2"), passed from the implanted subject via the headmount embodiments described previously and into the pre-amplifier cable) are attached electrically to the differential amplifier 840 providing the EEG signal 880 described previously. A double-pole-double-throw (DPDT) relay remains in its default configuration 870 in which the stimulation lines are electrically disconnected from both the electrodes poles 864, 868 and the differential amplifier 840. This prevents damage to the differential amplifier 840 and/or the inadvertent passage of stimulation or electrical noise to the animal.

Referring again to FIG. 1, when the stimulation control board 1086 receives a HIGH digital trigger 1084, the reed relay (described above) connects the stimulation lines carrying the electrical stimulation 1082 through to the lines carrying the neurostimulation 1032 into the pre-amp cable 1008 (via the electrical swivel 1010). The associated N-FET (described above) then disconnects the pre-amp control signals 1030 from ground, allowing the pre-amp control signals 1030 to become digital HIGH, switching the pre-amp cable 1008 into "stimulation" mode in which the stimulation is allowed to pass through to the animal as will be described.

Figure 8B:
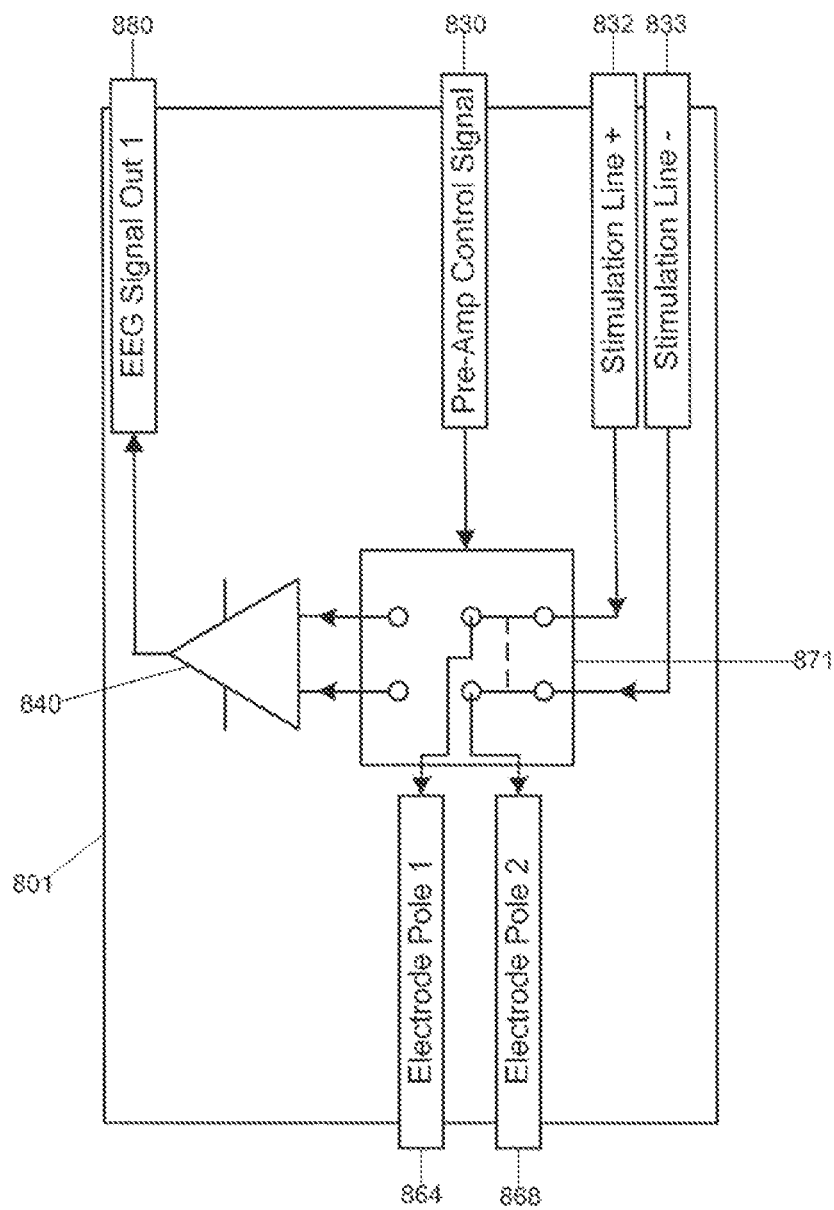
FIG. 8B is an additional block diagram of a circuit that may be used with a cable in a system in accordance with an embodiment.

Referring now to FIG. 8B, the pre-amplifier 801 when in "stimulation" mode, i.e., when the pre-amplifier control signal 830 is digital HIGH, the poles of the corresponding bipolar electrodes (first electrode pole 864 ("Electrode Pole 1") and second electrode pole 868 ("Electrode Pole 1") passed from the implanted subject via the headmount embodiments described previously and into the pre-amplifier cable) are disconnected electrically from the differential amplifier 840 (which is left open circuit) by the action of a DPDT in its switched configuration 871. This prevents stimulation from being applied to the inputs of the differential amplifier 840 and therefore damaging it or saturating the signal. The relay additionally serves to electrically connect the stimulation lines 832, 833 to the electrode poles 864 and 868, allowing stimulation to be passed back through the cable and headmount (as described previously) into the subject. Thus, the electrodes can be used for delivering stimulation without concern that the delivery of stimulation will destroy or swamp (e.g., saturate) the amplifiers so that they will not be available when sensing EEG signals after stimulation is desired to resume.

Figure 8C:
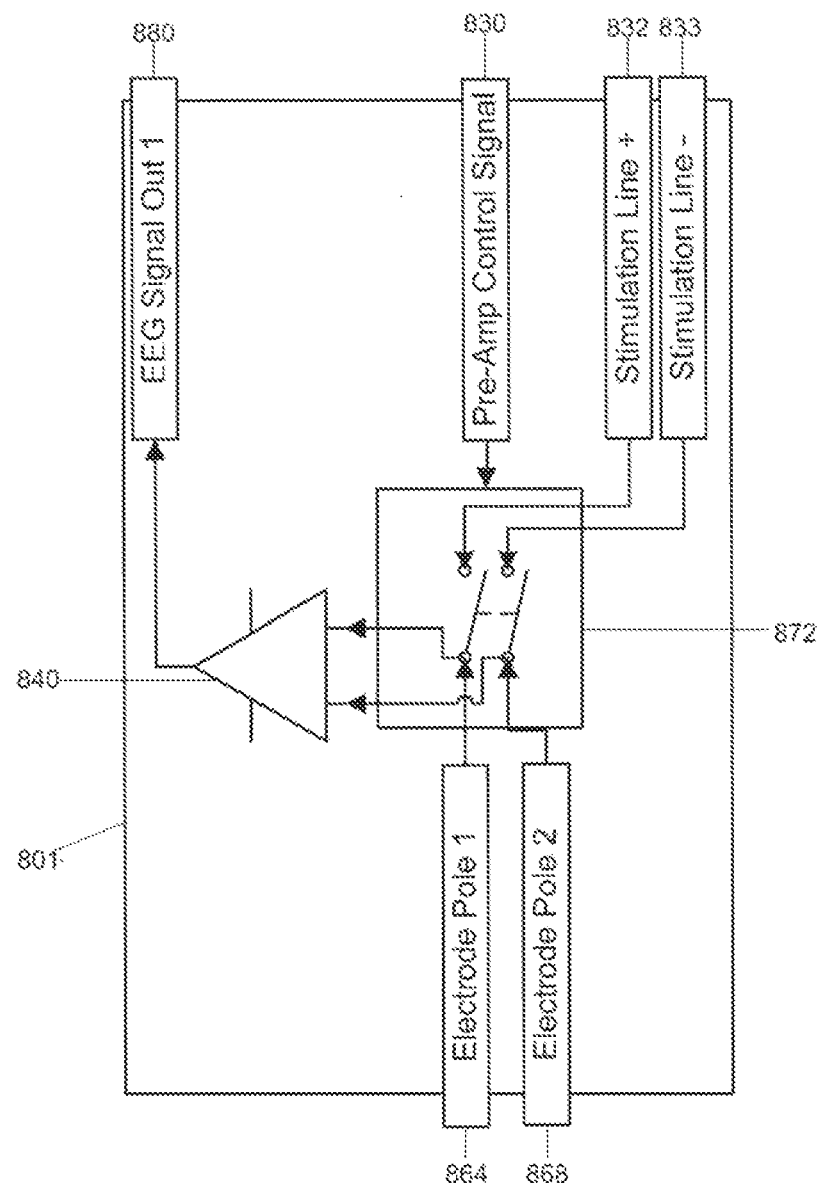
FIG. 8C is another block diagram of a circuit that may be used with a cable in a system in accordance with an embodiment.
Figure 8D:
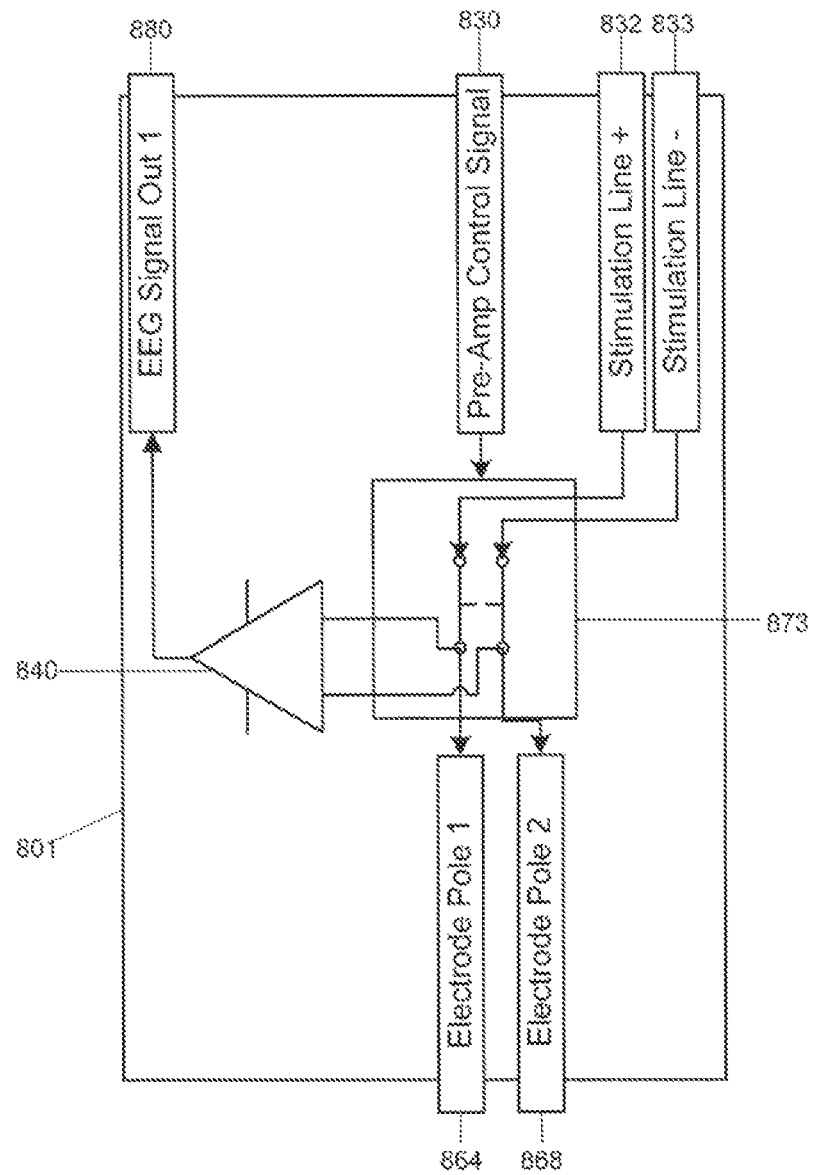
FIG. 8D is a further block diagram of a circuit that may be used with a cable in a system in accordance with an embodiment.

In FIG. 8C, an alternate method of protecting the differential amplifier 840 can be realized by making the differential amplifier inputs high impedance. When in "sense" mode, a double-pole-single-throw-relay (DPST) will remain in a default open circuit configuration 872, thus disconnecting the stimulation lines 832, 833 from the differential amplifier 840. This serves to eliminate stimulator noise from the stimulation lines 832, 833 from being amplified into the EEG signal. In FIG. 8D, when "stimulation" mode is desired and the pre-amplifier control signal 830 is made digital HIGH, the relay contacts become closed 873, thus connecting the stimulation lines 832 and 833 to the electrode poles 864 and 868, allowing stimulation to be delivered to the animal. In this method, the differential amplifier 840 is configured with high impedance input, thus allowing the stimulation to be delivered preferentially to the animal rather than to the higher impedance present on the inputs of the differential amplifier 840, thus protecting it from damage.

The schematics and methods in FIGS. 8A-80 are simplified representations of how such a system may achieve desired functionality. In an embodiment of a pre-amplifier configured as described above, multiple channels with duplicated circuitry may be provided allowing for multiple electrodes to independently switch from sense to stimulation mode with the application of the appropriate control signals.

Referring now to FIGS. 9A-9F, additional components of a system and experimental set up including a research animal enclosure 900 according to embodiments will now be described. The research animal enclosure 900 may be used in combination with a research subject (not shown in FIGS. 9A-9F) in which a headmount or headmount assembly in accordance with previously described embodiments has been installed and tethered to other components or equipment associated with the system located externally of the research animal enclosure 900. In some embodiments, the tethering may be accomplished, at least in part, by attaching a cable (such as the pre-amp cable 1008 described above in connection with FIG. 1 and FIGS. 8A-8D) at a distal end thereof to the headmount or headmount assembly and at a proximal end thereof to either to a commutator or mechanical swivel 930 provided in the research animal enclosure 900 or to other equipment or components external to the research animal enclosure 900.

In some embodiments, the research animal enclosure 900 is configured to enable EEG recording, electrical stimulation and video monitoring of a research subject while allowing the animals to remain ambulatory within the confines of the research animal enclosure 900. The EEG recording and electrical stimulation may be enabled through one or more cables (e.g., through a pre-amp cable 1008 described above in connection with FIG. 1 and FIGS. 8A-8D and/or a flexible braided cable 610 and/or the (latching) male connector 653 described in connection with FIGS. 6A-6F). Video monitoring and/of storage of video clips corresponding to the subject's behavior may be obtained with a video set up such as described above in connection with FIG. 1, including, for example, a video camera 1100 a video multiplexer 1102, and a video card 1104 to convert the video signals into a digital form.

In some embodiments, the research animal enclosure 900 (e.g., cage) is generally in the shape of a rectangular prism and is constructed of transparent material (e.g., from a clear acrylic sheet). The transparent material allows a clear visual path for observation of the animal within the enclosure, such as to facilitate video recording. The research animal enclosure 900 may be provided with a water bottle 901 and a mesh floor 903. A cut-out 914 may be provided for receiving a food hopper or some alternate structure, such as removable door 916 embedded with one or more plastic adapter nipple(s) 918 (e.g., plastic adapter nipples) for delivering a substance into the interior of the research animal enclosure 900, such as an anesthesia agent.

Another feature of some embodiments of the research animal enclosure 900 is the attachment of food and water delivery mechanisms (e.g., a water bottle) in an inconspicuous manner, such that said mechanisms will not obstruct monitoring of the animals. That is, the placement of the delivery mechanisms for food and water are out of the visual path used for video monitoring. The research animal enclosure 900 is generally free from occlusions and physically-limiting obstructions (e.g., such as might cause a wire, cable, connector, etc. to snag or become otherwise compromised through the normal movement of the animal.) Additionally, the way the food and water delivery mechanisms are mounted may provide physical support for (while maintaining accessibility of) the food and water mechanisms (such as a shelf and bracket to support the water bottle 901 that is inverted for a rat from which to drink, or an attachment point for securing a food hopper in place).

Still another embodiment of a research animal enclosure 900 has a feature comprising an access door 904 that is large and mounted in a side of a main body of the enclosure. The access door 904 provides personnel with a spacious means of accessing the enclosed animal. Such an access door may be mounted with hinges 906 or track-mounted (or mounted by an otherwise suitable means), such that the access door 904 avoids (or supplies) visual occlusion relative to a video monitoring system.

Figure 9A:
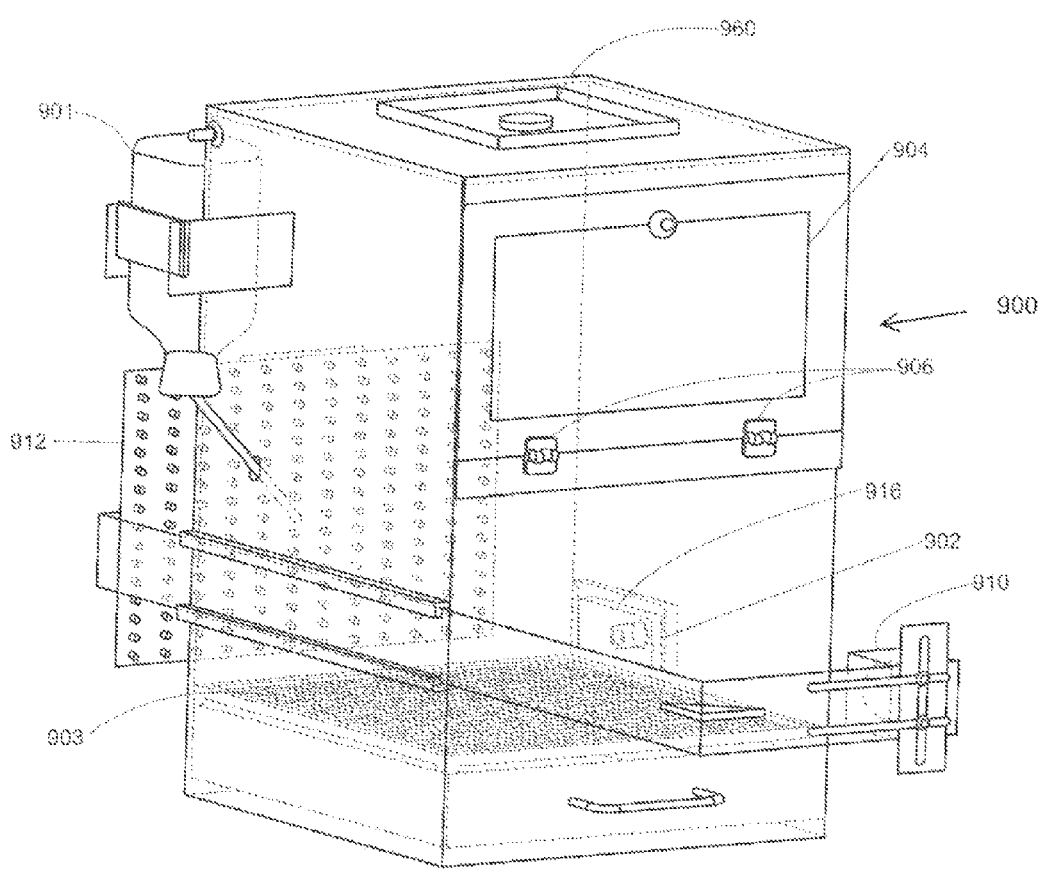
FIG. 9A is a perspective view of a research animal enclosure for use with a system according to an embodiment.
Figure 9B:
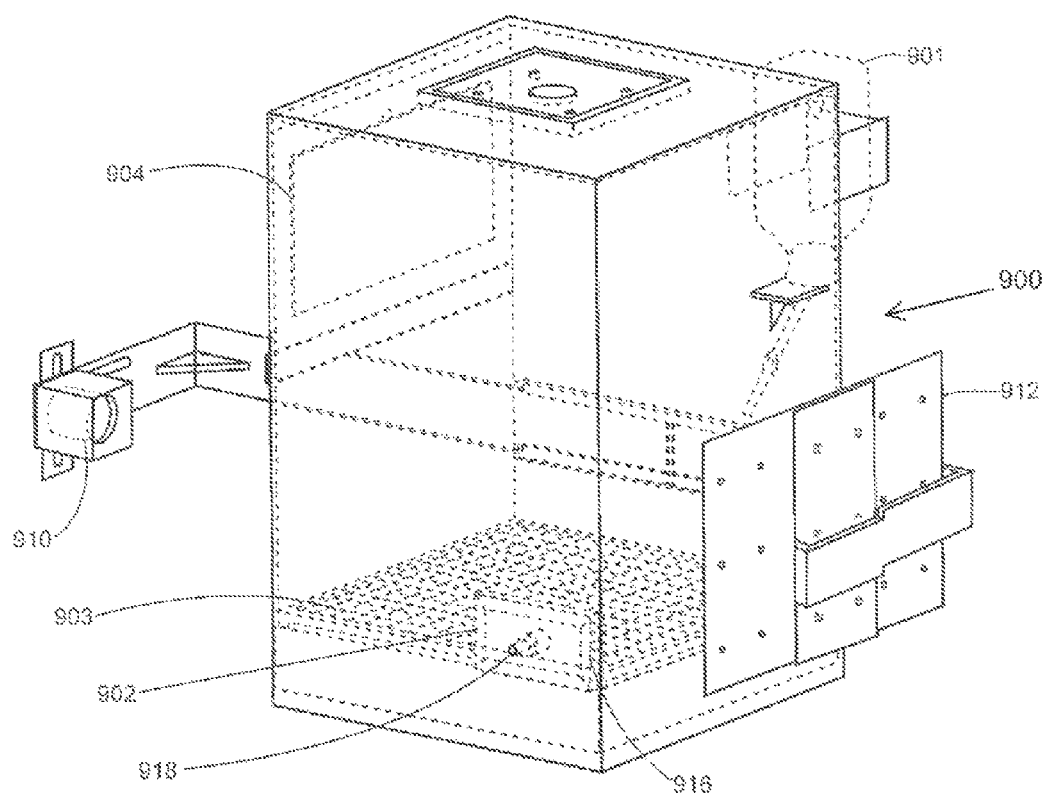
FIG. 9B is an alternate perspective view of the animal enclosure of FIG. 9A.

A video camera 910 may be provided and associated with the research animal enclosure 900 as shown in FIG. 9A for monitoring of the subjects (described below) and one or more LED light panels 912 may be provided in the research animal enclosure 900 to supply backlighting for video recording.

Figure 9C:
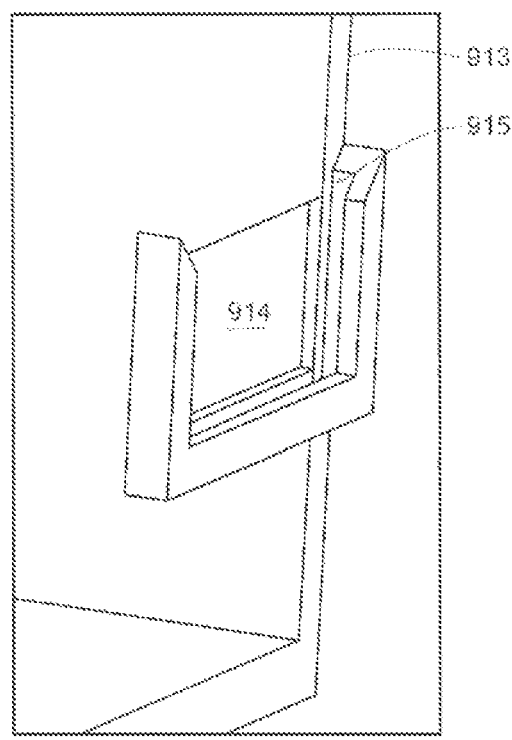
FIG. 9C is a zoomed in view of a portion of the animal enclosure of FIG. 9A.

FIG. 9C is a zoomed-in view of a portion of an research animal enclosure 900 according to an embodiment in which a cut-out 914 is provided having a track 915. The cut-out 914 and track 915 may be configured to receive a food hopper or other structure such as a removable door 916 fitted with a plastic adapter nipple 918 for delivering an anesthesia gas to the subject. In some embodiments, the cut-out 914 may be provided with a generally rectangular shape in a side wall 913 of the research animal enclosure 900.

Figure 9D:
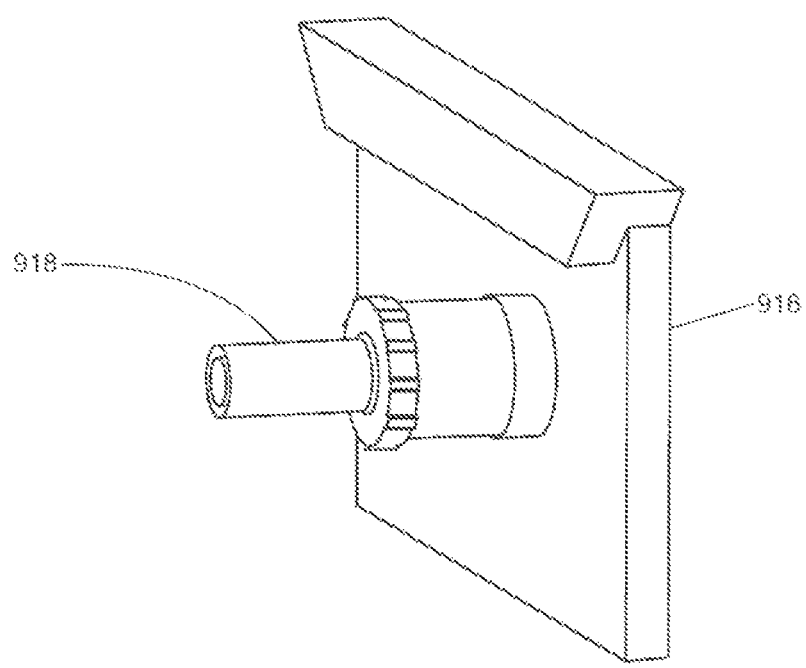
FIG. 9D is a removable door that can be used with the animal enclosure of FIG. 9A.

FIG. 9D illustrates one example of a removable door 916 in accordance with an embodiment that may be configured to be received in a cut-out 914 provided in a side wall 913 of a research animal enclosure 900. The removable door 916 is provided with a plastic adapter nipple 918, which may be formed from plastic or another suitable material. In some embodiments, the plastic adapter nipple 918 may be used to deliver something into the research animal enclosure 900 (e.g., anesthesia gas) or to otherwise make a substance available to the rat. When the removable door 916 is removed, it may be replaced with a food hopper or a blank in order to close off the cut-out 914 from the environment external to the research animal enclosure 900.

Figure 9E:
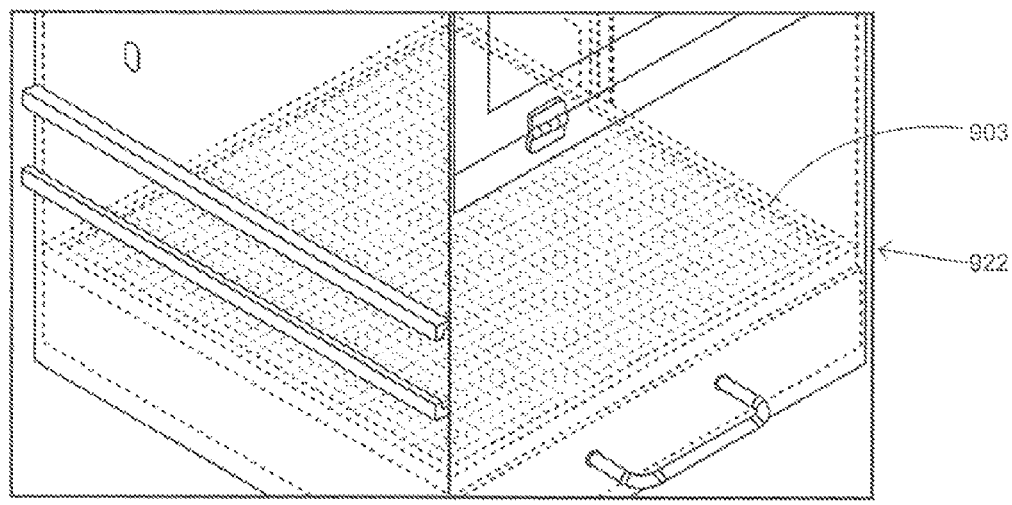
FIG. 9E is perspective view of a bottom portion of the animal enclosure of FIG. 9A.
Figure 9F:
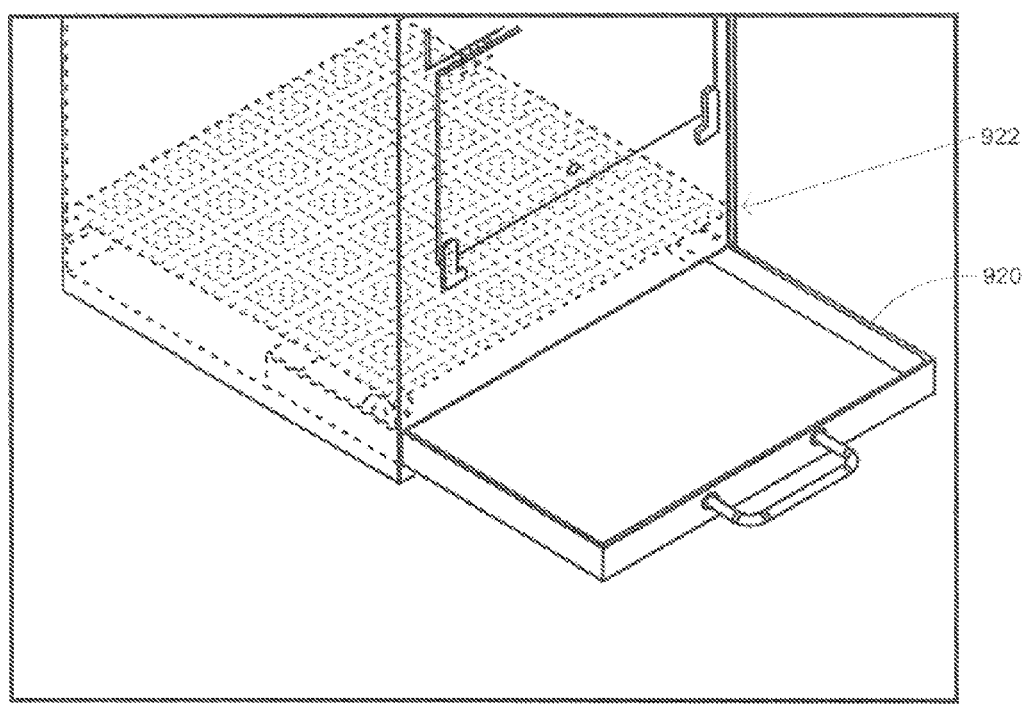
FIG. 9F is an exploded perspective view of the portion of the animal enclosure of FIG. 9E.

Referring now to FIG. 9E-9F, embodiments of the research animal enclosure 900 may be provided with a waste removal system. The waste removal system allows animal waste to be removed regularly without the trouble of having to relocate the animal and/or cease monitoring. In an embodiment, a bottom portion of the research animal enclosure 900 is provided as a mesh floor 903 of resilient material (e.g., stainless steel) with sufficient gap size as to allow animal waste to pass through rather than accumulate. Optionally, the waste removal system may include a removable drawer 920 mounted beneath the mesh floor 903 in such a fashion as to remain accessible and inconspicuous when used in conjunction with any extension arms (discussed below in connection with FIG. 9H). Such a removable drawer 920 may be lined with absorbent bedding materials to facilitate cleaning.

Figure 9G:
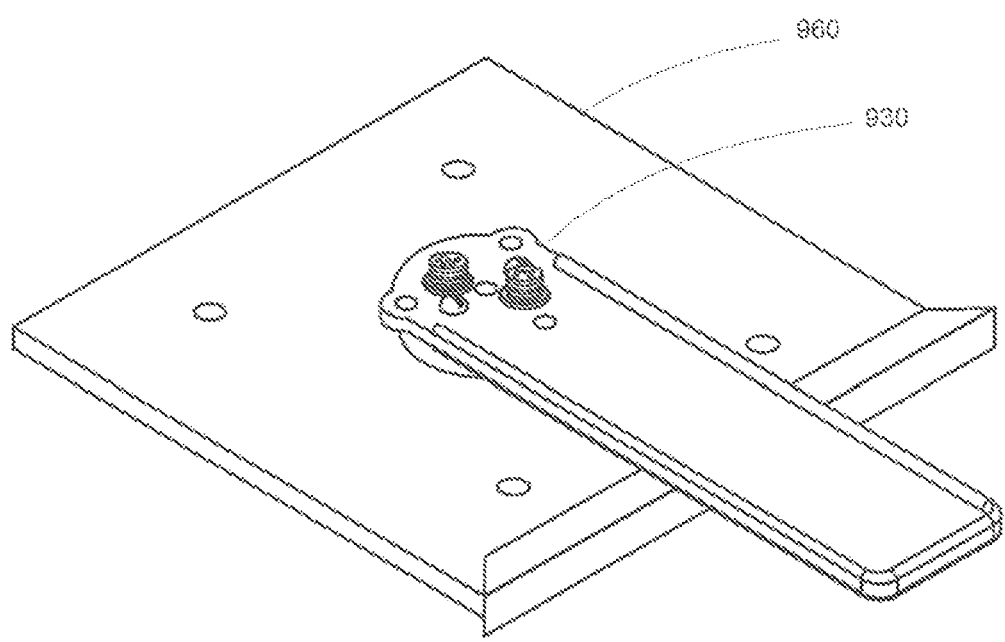
FIG. 9G is a perspective view of a top portion of an animal enclosure in accordance with an embodiment.

In some embodiments of a research animal enclosure 900, as shown in FIG. 9G, a commutator or mechanical swivel 930 may be provided in a top portion 960 of the research animal enclosure 900. The mechanical swivel 930 (e.g., commutator) is provided with features that allow electrical connections to be made and maintained between a cable (such as the pre-amp cable 1008 described in connection with FIG. 1 and FIGS. 8A-8D above) and/or other elements of the experimental set up that may be located outside of the enclosure. In other embodiments, a commutator is provided with features that allow fluid transmission or optical connection to be made and maintained between a cable and the other elements of the experimental set up that may be located outside of the enclosure.

Figure 9H:
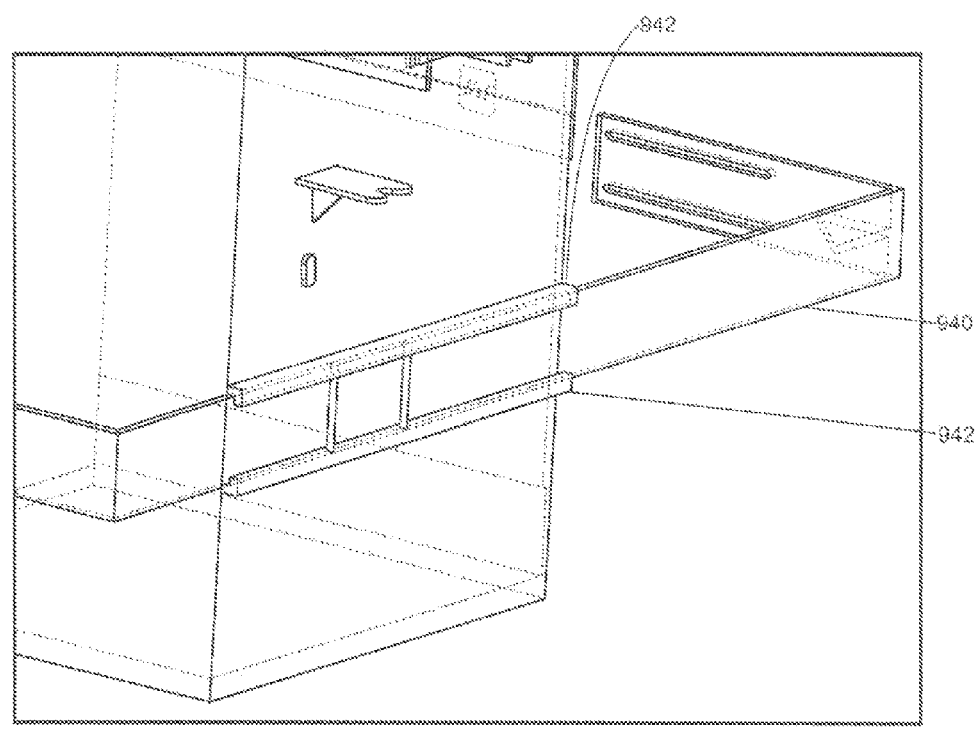
FIG. 9H is a perspective view of a portion of an animal enclosure of FIG. 9A.

In some embodiments of a research animal enclosure 900, as shown in FIG. 9H, an extension arm 940 may be provided to which accessories, such as a video camera 910 and an LED light panel 912 may be attached or otherwise associated with the research animal enclosure 900. The extension arm 940 may be attached to a main body of the research animal enclosure 900 by any suitable means. In an embodiment, an extension arm track 942 may be permanently affixed to a side wall of the research animal enclosure 900, and a portion of the extension arm 940 is fitted into the extension arm track 942.

The extension arm 940 may be provided with a positioning mechanism (not shown) that allows the position in space of any attached accessory (e.g., a video camera 910) to be adjusted in three dimensions and temporarily fixed in place by a suitable means. In an embodiment, this can be accomplished by friction provided by a combination of knurled nuts and lock washers, mounted on threaded rods, the tightening of which will compress adjacent portions of the position mechanism. Loosening the knurled nuts, etc., allows for the cessation of applied friction and thus a re-positioning of the mechanism. To the end of the position mechanism may be attached accessories such as a video camera (see also FIGS. 9A-9B). In an embodiment, the position mechanism will allow a video camera 910 to be placed in such a fashion as to provide optimal picture for analysis purposes. (One suitable video camera may be a commercially-available camera sold by CleverSys, Inc.). An additional extension arm 940 may beneficially be used in conjunction with one or more LED light panels 912 (see also FIGS. 9A-9B) to provide backlighting of the animal in the research animal enclosure and to further optimize the video for analysis purposes.

Various example embodiments are thus described. All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein. Rather, the scope and spirit is embodied by the appended claims.

What is claimed is:

1. A headmount for use with a non-human subject comprising:
   a frame comprising a structural support configured to mount on a subject's cranium, the frame further comprising a top surface;
   a headstage comprising a hollow interior portion in which at least one circuit board and a connector in operable communication with the at least one circuit board is disposed, the headstage further comprising a lower surface; wherein the at least one circuit board is provided with elements configured to permit electrical connection with at least one electrode configured to be implanted in the subject; and
   a connection mechanism configured to establish a mechanical connection between the frame and the headstage, and to facilitate movement of the headmount between a closed arrangement wherein at least a portion of the top surface of the frame is in contact with at least a portion of the lower surface of the headstage, and an opened arrangement wherein the top surface of the frame is not in contact with the lower surface of the headstage.

2. The headmount of claim 1 wherein the mechanical connection mechanism is a hinge.

3. The headmount of claim 2 wherein the hinge further comprises a first set of half-hinge elements provided on a surface of the frame and a second set of half-hinge elements provided on surface of the headstage, wherein the headmount is configured so that the first set of half-hinge elements can mate with the second set of half-hinge elements.

4. The headmount of claim 3 wherein the hinge further comprises a removable rod configured to be removably inserted into a generally cylindrical aperture formed by the mating of the first set of half-hinge elements with the second set of half-hinge elements.

5. The headmount of claim 1 wherein the frame and at least a portion of the headstage are formed from a plastic.

6. The headmount of claim 1 wherein the connector comprises a first connector that is configured to mate with a second connector.

7. The headmount of claim 1 wherein the at least one circuit board further comprises a first circuit board spaced apart and a second circuit board wherein the first circuit board is spaced apart from the second circuit board by at least one spacing element.

8. The headmount of claim 7 wherein the at least one spacing element is configured to provide structural support for the combination of the first and second circuit boards.

9. The headmount of claim 7 wherein the at least one spacing element is a wire.

10. The headmount of claim 1 wherein the at least one circuit board includes electrical components suitable for acquiring a signal corresponding to electrographic activity of the subject.

11. The headmount of claim 10 wherein the electrical components are configured to communicate with electrically conductive elements configured to be implanted in the subject.

12. The headmount of claim 1, wherein:
the frame further comprises an outer surface defining a perimeter;
the headstage further comprises an outer surface defining a perimeter; and
the perimeter of the frame substantially matches the perimeter of the headstage.

13. The headmount of claim 1, wherein the frame comprises an anterior portion having a width and a posterior portion having a width, and the width of posterior portion is greater than the width of the anterior portion.

14. The headmount of claim 1, further comprising a securing mechanism configured to secure the headstage to the frame when the headmount is in a closed arrangement.

15. The headmount of claim 1, wherein the headstage comprises a connector aperture through which the connector passes.

16. The headmount of claim 15, wherein the headstage comprises a cutout that provides access to the connector aperture.

17. The headmount of claim 1, wherein the at least one printed circuit board is positioned on the lower surface of the headstage.

* * * * *